US008894711B2

(12) United States Patent
Varela

(10) Patent No.: US 8,894,711 B2
(45) Date of Patent: *Nov. 25, 2014

(54) EXPANDABLE INTERVERTEBRAL IMPLANT AND ASSOCIATED SURGICAL METHOD

(75) Inventor: Armando Varela, Boca Raton, FL (US)

(73) Assignee: Innova Spinal Technologies, LLC, Plantation, FL (US)

( * ) Notice: Subject to any disclaimer, the term of this patent is extended or adjusted under 35 U.S.C. 154(b) by 263 days.

This patent is subject to a terminal disclaimer.

(21) Appl. No.: 13/432,270

(22) Filed: Mar. 28, 2012

(65) Prior Publication Data

US 2012/0185049 A1    Jul. 19, 2012

Related U.S. Application Data

(63) Continuation-in-part of application No. 12/974,511, filed on Dec. 21, 2010, now Pat. No. 8,795,366.

(60) Provisional application No. 61/293,997, filed on Jan. 11, 2010, provisional application No. 61/296,932, filed on Jan. 21, 2010.

(51) Int. Cl.
*A61F 2/44* (2006.01)
*A61F 2/46* (2006.01)
*A61F 2/30* (2006.01)

(52) U.S. Cl.
CPC .............. *A61F 2/447* (2013.01); *A61F 2/4611* (2013.01); *A61F 2002/30281* (2013.01); *A61F 2002/30387* (2013.01); *A61F 2002/30507* (2013.01); *A61F 2002/30522* (2013.01); *A61F 2002/30538* (2013.01); *A61F 2002/30551* (2013.01); *A61F 2002/30556* (2013.01); *A61F 2002/30579* (2013.01); *A61F 2002/30841* (2013.01); *A61F 2002/30878* (2013.01); *A61F 2002/30904* (2013.01); *A61F 2002/4623* (2013.01); *A61F 2002/4627* (2013.01); *A61F 2002/3039* (2013.01); *A61F 2002/30397* (2013.01); *A61F 2002/304* (2013.01); *A61F 2002/30434* (2013.01); *A61F 2002/30616* (2013.01); *A61F 2002/30827* (2013.01); *A61F 2002/4624* (2013.01); *A61F 2002/30601* (2013.01)
USPC ...................................... 623/17.16

(58) Field of Classification Search
CPC ..................... A61F 2/44–2/447; A61F 2/4611
USPC ........................ 623/17.11–17.16; 606/99, 105
See application file for complete search history.

(56) References Cited

U.S. PATENT DOCUMENTS 6,102,950 A * 8/2000 Vaccaro ..................... 623/17.16
6,454,807 B1  9/2002 Jackson
6,685,742 B1  2/2004 Jackson (Continued)

*Primary Examiner* — Mary Hoffman
*Assistant Examiner* — Michelle C Eckman
(74) *Attorney, Agent, or Firm* — Clements Bernard PLLC; Christopher L. Bernard; Lawrence A. Baratta, Jr.

(57) ABSTRACT

The present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member from the inferior member; wherein the expansion mechanism includes a proximal wedge structure and a distal wedge structure that are relatively translated between the superior member and the inferior member, wherein the proximal wedge structure and the distal wedge structure are each coupled to the superior member and the inferior member by a plurality of aligned and/or staggered (i.e. nested) track structures and rail structures.

16 Claims, 49 Drawing Sheets

(56) References Cited

U.S. PATENT DOCUMENTS

| | | |
|---|---|---|
| 6,706,070 B1 | 3/2004 | Wagner et al. |
| 6,835,206 B2 | 12/2004 | Jackson |
| 7,569,074 B2 | 8/2009 | Eisermann et al. |
| 7,771,473 B2 | 8/2010 | Thramann |
| 8,105,382 B2 | 1/2012 | Olmos et al. |
| 2005/0131536 A1 | 6/2005 | Eisermann et al. |
| 2005/0278026 A1 | 12/2005 | Gordon et al. |
| 2006/0247770 A1 | 11/2006 | Peterman |
| 2008/0140207 A1* | 6/2008 | Olmos et al. ............... 623/17.16 |
| 2008/0147193 A1* | 6/2008 | Matthis et al. ............. 623/17.16 |
| 2009/0024217 A1* | 1/2009 | Levy et al. ................. 623/17.16 |
| 2010/0211176 A1* | 8/2010 | Greenhalgh ................ 623/17.15 |
| 2010/0222884 A1* | 9/2010 | Greenhalgh ................ 623/17.11 |
| 2010/0292796 A1* | 11/2010 | Greenhalgh et al. ....... 623/17.11 |
| 2011/0054621 A1* | 3/2011 | Lim .......................... 623/17.16 |
| 2011/0144755 A1* | 6/2011 | Baynham et al. .......... 623/17.16 |
| 2012/0059470 A1* | 3/2012 | Weiman .................... 623/17.11 |
| 2012/0059475 A1* | 3/2012 | Weiman .................... 623/17.16 |
| 2012/0203347 A1* | 8/2012 | Glerum et al. ............ 623/17.16 |

* cited by examiner

EXPANDABLE INTERVERTEBRAL IMPLANT AND ASSOCIATED SURGICAL METHOD

CROSS-REFERENCE TO RELATED APPLICATION(S)

The present patent application/patent is a continuation-in-part (CIP) of co-pending U.S. patent application Ser. No. 12/974,511, filed on Dec. 21, 2010, and entitled "EXPANDABLE INTERVERTEBRAL IMPLANT AND ASSOCIATED SURGICAL METHOD," which claims the benefit of priority of U.S. Provisional Patent Application No. 61/293,997, filed on Jan. 11, 2010, and entitled "EXPANDABLE INTERVERTEBRAL BODY STABILIZATION DEVICES AND ASSOCIATED SURGICAL METHODS" and U.S. Provisional Patent Application No. 61/296,932, filed on Jan. 21, 2010, and entitled "EXPANDABLE INTERVERTEBRAL BODY STABILIZATION DEVICES AND ASSOCIATED SURGICAL METHODS," the contents of all of which are incorporated in full by reference herein.

FIELD OF THE INVENTION

The present invention relates generally to minimally-invasive, surgically-implantable spinal devices and systems. More specifically, the present invention relates to an expandable intervertebral implant that is surgically implanted to, in-situ, distract, realign, and/or stabilize or fuse a portion of the spine of a patient in the treatment of injury, disease, and/or degenerative condition. Exemplary indications include, but are not limited to, spinal stenosis, degenerative disc disease with a loss of disc height, disc herniation, spondylolisthesis, retrolisthesis, and disogenic back pain. This expandable intervertebral implant may be surgically implanted via an open or, more preferably, a minimally-invasive surgical procedure. Advantageously, the expandable intervertebral implant has both a very small undeployed vertical cross-section and a very small undeployed horizontal footprint due to the use of superior and inferior members that nest against one another in a novel manner.

BACKGROUND OF THE INVENTION

In various cases, it is desirable to restore the anatomic relationship between various vertebral elements, thereby re-establishing spinal stability, by means other than conventional monolithic and/or multi-piece interbody spacers. Typically, these devices require sizable working channels, soft tissue disruption, nerve root retraction, and significant bone resection, thereby increasing the resulting stress on other vertebral elements. Further, morbidities associated with these more-invasive procedures include, but are not limited to, greater blood loss, longer recovery, and increased risk of surgical site infection.

In such cases, the use of an alternative intervertebral implant, especially one compatible with minimally-invasive surgical techniques, is desirable. An intervertebral implant that expands in-situ would allow implantation without the iatrogenic insult that is commonly associated with the implantation of conventional monolithic and/or multi-piece interbody spacers in a minimally-invasive manner. However, no such alternative devices or systems are currently available, at least not any that are adequate.

BRIEF SUMMARY OF THE INVENTION

In various exemplary embodiments, the present invention provides an expandable intervertebral implant that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant includes a superior member and an inferior member, each of which has a partially or substantially wedge or prismatic shape and a partially or substantially convex or other-shaped surface that is suitable for engaging the substantially concave surfaces of the associated bony superior and inferior intervertebral endplates. Optionally, the superior member and the inferior member are each thinner at the leading edge of the expandable intervertebral implant than they are at the trailing edge of the expandable intervertebral implant, such that insertion into the intervertebral space may be aided, although this is not a requirement and the expandable intervertebral implant may have a uniform thickness, when undeployed, from the leading edge to the trailing edge. For similar reasons, the leading edge of the both the superior member and the inferior member may have a knifed or rounded shape. Once disposed in the intervertebral space, the expandable intervertebral implant is actuated and deployed, with the superior member and the inferior member moving apart from one another, seating against the associated intervertebral endplates, and distracting, realigning, and/or stabilizing them to a desired degree. In order to ensure that the expandable intervertebral implant is held securely in the intervertebral space, the external surface of each of the superior member and the inferior member is provided with a plurality of ridges or other friction structures, providing purchase with the associated intervertebral endplates.

When undeployed, the superior member and the inferior member are configured such that they nest against one another, thereby providing the undeployed expandable intervertebral implant with the smallest possible form factor for insertion through the skin and musculature of the patient and into the intervertebral space. In the exemplary embodiment provided, this is accomplished via the use of cut-away sections associated with the superior member and the inferior member, not unlike a tongue-in-groove joint assembly. The combined total height of the superior member and the inferior member when nested together in the undeployed state is less than the sum of the heights of the superior member and the inferior member individually. This is accomplished via a plurality of nesting ramp structures and/or other angled surfaces associated with the superior member and/or the inferior member that selectively cause distraction/separation of the superior member and the inferior member via interaction with a translating wedge structure. These various ramp structures are offset (i.e. staggered) in such a manner that the form factor of the expandable intervertebral implant is minimized when undeployed.

In one exemplary embodiment, the present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member. The expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track (i.e. channel) and rail system. The expansion mechanism disposed between the superior member and the inferior member may also be configured to selectively translate the superior member with respect to the inferior member.

In another exemplary embodiment, the present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member, wherein the expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track and rail system. The expansion mechanism disposed between the superior member and the inferior member may also be configured to selectively translate the superior member with respect to the inferior member.

In a further exemplary embodiment, the present invention provides a spinal surgical method, including: providing an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member and the inferior member; disposing the expandable intervertebral implant between the superior intervertebral body and the inferior intervertebral body; and selectively adjusting the separation of the superior member and the inferior member, thereby selectively adjusting a distraction of the superior intervertebral body from the inferior intervertebral body. The expansion mechanism includes a wedge structure that is translated between the superior member and the inferior member. The expansion mechanism also includes a screw that is coupled to the wedge structure and causes the wedge structure to translate when rotated. One or more of the superior member and the inferior member include a ramp structure on their opposed faces. Interaction of the wedge structure and the ramp structure of the one or more of the superior member and the inferior member as the wedge structure is translated causes adjustment of the separation of the superior member and the inferior member. The superior member is coupled to the inferior member through the wedge structure and the ramp structure of the one or more of the superior member and the inferior member. Optionally, the superior member is coupled to the inferior member via a track and rail system. The expansion mechanism disposed between the superior member and the inferior member may also be configured to selectively translate the superior member with respect to the inferior member.

In a still further exemplary embodiment, the present invention provides an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member from the inferior member; wherein the expansion mechanism includes a proximal wedge structure and a distal wedge structure that are relatively translated between the superior member and the inferior member, wherein the proximal wedge structure and the distal wedge structure are each coupled to the superior member and the inferior member by a plurality of track structures and rail structures. One or more track structures and rail structures associated with a top surface of the distal wedge structure are offset horizontally with respect to one or more track structures and rail structures associated with a bottom surface of the distal wedge structure. One or more track structures and rail structures associated with a top surface of the proximal wedge structure are aligned horizontally with respect to one or more track structures and rail structures associated with a bottom surface of the proximal wedge structure. The expansion mechanism also includes an actuation bolt that passes through the proximal wedge structure and is coupled to the distal wedge structure and causes the wedge structures to relatively translate when rotated. The superior member and the inferior member each include a plurality of ramp structures on their opposed faces. The superior member includes a ramp structure that engages the proximal wedge structure and a ramp structure that engages the distal wedge structure. The inferior member includes a ramp structure that engages the proximal wedge structure and a ramp structure that engages the distal wedge structure. The expandable intervertebral implant also includes a plurality of elongate arm structures protruding from the superior member and the inferior member and engaging a corresponding recess of the other component.

In a still further exemplary embodiment, the present invention provides a surgical method including providing an expandable intervertebral implant, including: a superior member configured to engage a superior intervertebral body; an inferior member configured to engage an inferior intervertebral body; and an expansion mechanism disposed between the superior member and the inferior member configured to selectively adjust a separation of the superior member from the inferior member; wherein the expansion mechanism includes a proximal wedge structure and a distal wedge structure that are relatively translated between the superior member and the inferior member, wherein the proximal wedge structure and the distal wedge structure are each coupled to the superior member and the inferior member by a plurality of track structures and rail structures. One or more track structures and rail structures associated with a top surface of the distal wedge structure are offset (i.e. staggered) horizontally with respect to one or more track structures and rail structures associated with a bottom surface of the distal wedge structure. One or more track structures and rail structures associated with a top surface of the proximal wedge structure are aligned horizontally with respect to one or more track structures and rail structures associated with a bottom surface of the proximal wedge structure. Alternatively, one or more track structures and rail structures associated with a top surface of the proximal wedge structure are offset (i.e. staggered) horizontally with respect to one or more track structures and rail structures associated with a bottom surface of the proximal wedge structure. The expansion mechanism also includes an actuation bolt that passes through the proximal wedge structure and is coupled to the distal wedge structure and causes the wedge structures to relatively translate when rotated. The superior member and the inferior member each include a plurality of ramp structures on their opposed faces. The superior member includes a ramp structure that engages the proximal wedge structure and a ramp structure that engages the distal wedge structure. The inferior member includes a ramp structure that engages the proximal wedge structure and a ramp structure that engages the distal wedge structure. The expandable intervertebral implant also includes a plurality of elongate arm structures protruding from the superior member and the inferior member and engaging a corresponding recess of the other component.

BRIEF DESCRIPTION OF THE DRAWINGS

The expandable intervertebral implant of the present invention is illustrated and described herein with reference to the various drawings, in which like reference numbers are used to denote like device components, as appropriate, and in which.

DETAILED DESCRIPTION OF THE INVENTION

Figure 1:
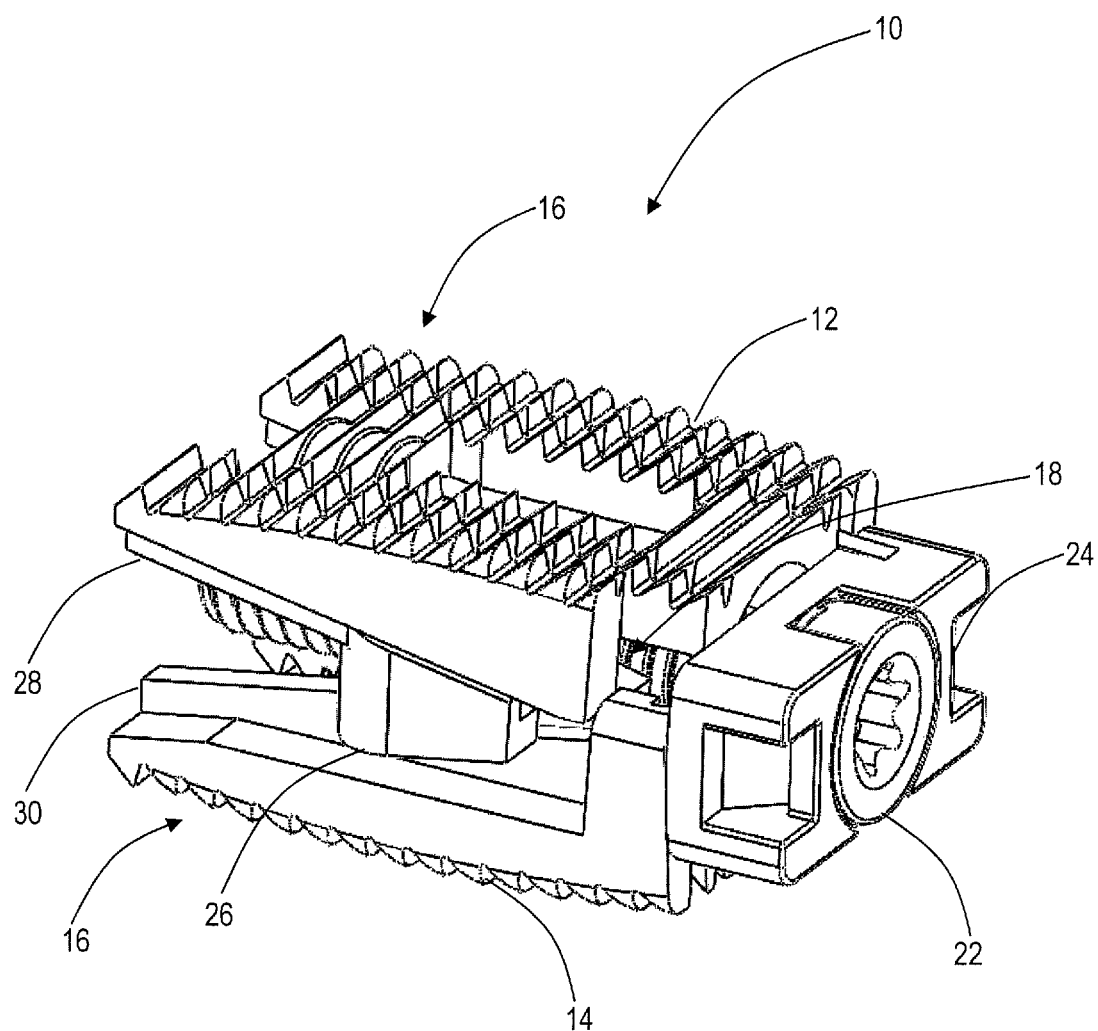
FIG. 1 is a perspective view of one exemplary embodiment of the expandable intervertebral implant of the present invention.

Referring to FIG. 1, in one exemplary embodiment, the present invention provides an expandable intervertebral implant 10 that is selectively disposed in the intervertebral space and deployed, thereby in-situ distracting, realigning, and/or stabilizing or fusing a portion of the spine of a patient in the treatment of injury, disease, and/or degenerative condition. The expandable intervertebral implant 10 includes a superior member 12 and an inferior member 14, each of which has a partially or substantially wedge or prismatic shape and a partially or substantially convex or other-shaped surface that is suitable for engaging the substantially concave surfaces of the associated bony superior and inferior intervertebral endplates. Optionally, the superior member 12 and the inferior member 14 are each thinner at the leading edge of the expandable intervertebral implant 10 than they are at the trailing edge of the expandable intervertebral implant 10, such that insertion into the intervertebral space may be aided, although this is not a requirement and the expandable intervertebral implant 10 may have a uniform thickness, when undeployed, from the leading edge to the trailing edge. For similar reasons, the leading edge of the both the superior member 12 and the inferior member 14 may have a knifed or rounded shape. Once disposed in the intervertebral space, the expandable intervertebral implant 10 is actuated and deployed, with the superior member 12 and the inferior member 14 moving apart from one another, seating against the associated intervertebral endplates, and distracting, realigning, and/or stabilizing them to a desired degree. The mechanisms by which this happens are described in greater detail herein below. This operation is analogous to placing a jack under a car, positioning it appropriately, snugging it in the space beneath the car, and then jacking it up. In order to ensure that the expandable intervertebral implant 10 is held securely in the intervertebral space, the external surface of each of the superior member 12 and the inferior member 14 is provided with a plurality of ridges 16 or other friction structures, providing purchase with the associated intervertebral endplates. The overall dimensions of the expandable intervertebral implant 10 are on the order of several millimeters to tens of millimeters, such that a set of implants containing a series of incremental implant sizes can provide a height expansion range of 7-18 mm or more than 3-5 mm each, for example. Other suitable dimensions may, of course, be utilized.

When undeployed, the superior member 12 and the inferior member 14 are configured such that they nest against one another, thereby providing the undeployed expandable intervertebral implant 10 with the smallest possible form factor (i.e. smallest possible undeployed vertical cross-section and smallest/shortest possible undeployed horizontal footprint) for insertion through the skin and musculature of the patient and into the intervertebral space. In the exemplary embodiment illustrated in FIG. 1, this is accomplished via the use of cut-away sections 18 and 20 associated with the superior member 12 and the inferior member 14.

By way of overview, the superior member 12 and the inferior member 14 are actuated via the rotation of a screw 22 disposed through a housing 24 located at the trailing edge of the expandable intervertebral implant 10. This screw 22 is disposed along the central axis of the expandable intervertebral implant 10, between the superior member 12 and the inferior member 14. The screw 22 engages an internally-threaded wedge structure 26 disposed between the superior member 12 and the inferior member 14, selectively translating the wedge structure 26 along the central axis of the expandable intervertebral implant 10 with rotation. This translation causes the wedge structure 26 to interact with an associated wedge shape or structure of the superior member 12 and/or inferior member 14, thereby forcing the superior member 12 and the inferior member 14 apart/together with translation of the wedge structure 26. Preferably, the superior member 12 and the inferior member 14 each include a track structure 28 and 30, thereby securely coupling the superior member 12 to the inferior member 14 through the wedge structure 26. The interaction of the wedge structure 26 with the wedge shape or structure of the superior member 12 and/or inferior member 14 during translation preferably causes the superior member 12 and the inferior member 14 to move apart/together while maintaining a substantially parallel relationship. Alternatively, the superior member 12 and the inferior member 14 may move apart with a predetermined lordotic angle. The superior member 12 and the inferior member 14 may move apart in a substantially-continuous fashion, or they may move apart in 0.5-mm or smaller increments, for example. In addition, the interaction of the wedge structure 26, the superior member 12, and the inferior member 14 may be designed such that as the superior member 12 and the inferior member 14 move apart, they also translate with respect to one another. This is helpful in, for example, ensuring that the plurality of ridges 16 or other friction structures are securely seated in the bony material.

Figure 2:
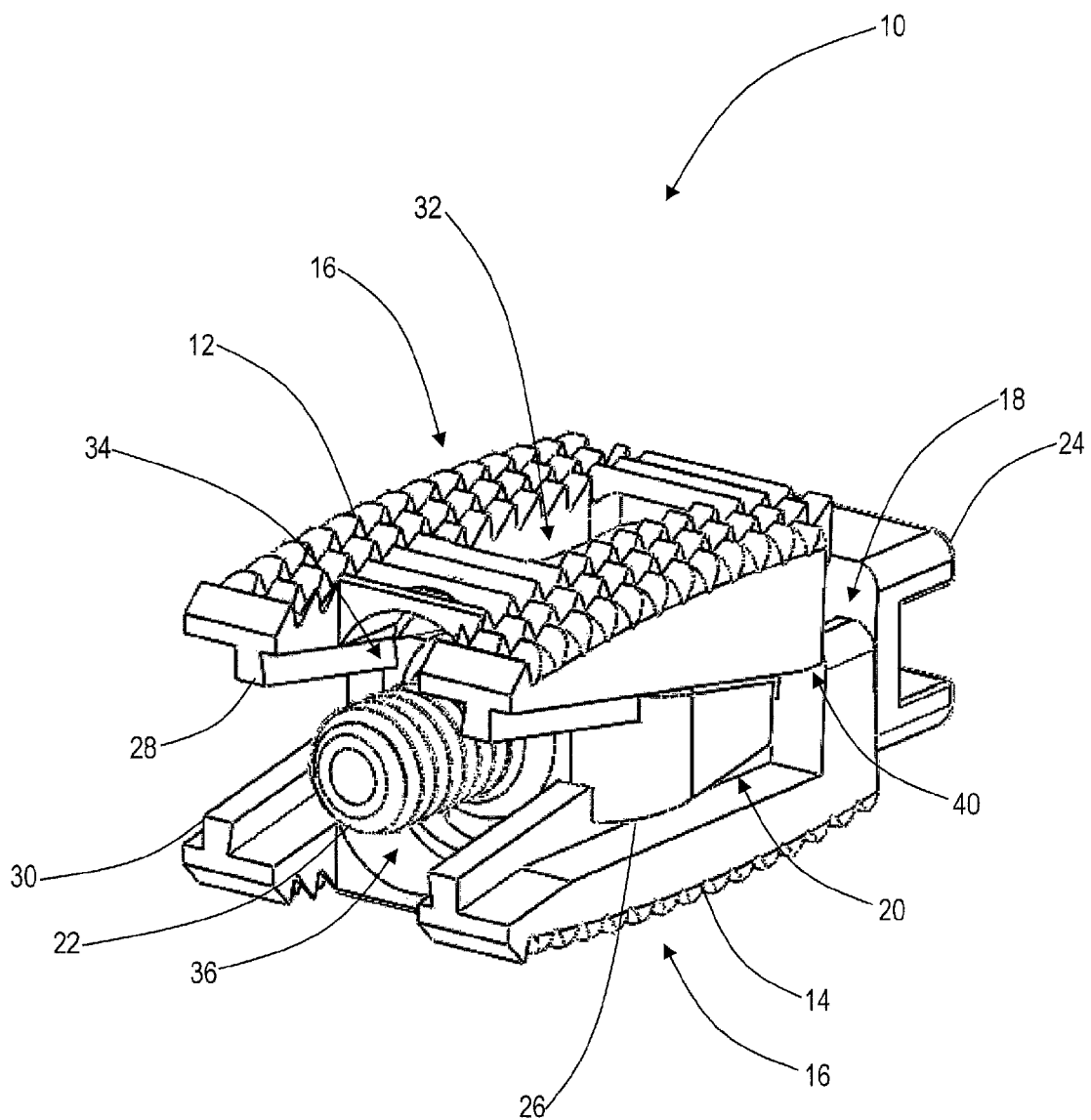
FIG. 2 is another perspective view of one exemplary embodiment of the expandable intervertebral implant of the present invention.
Figure 3:
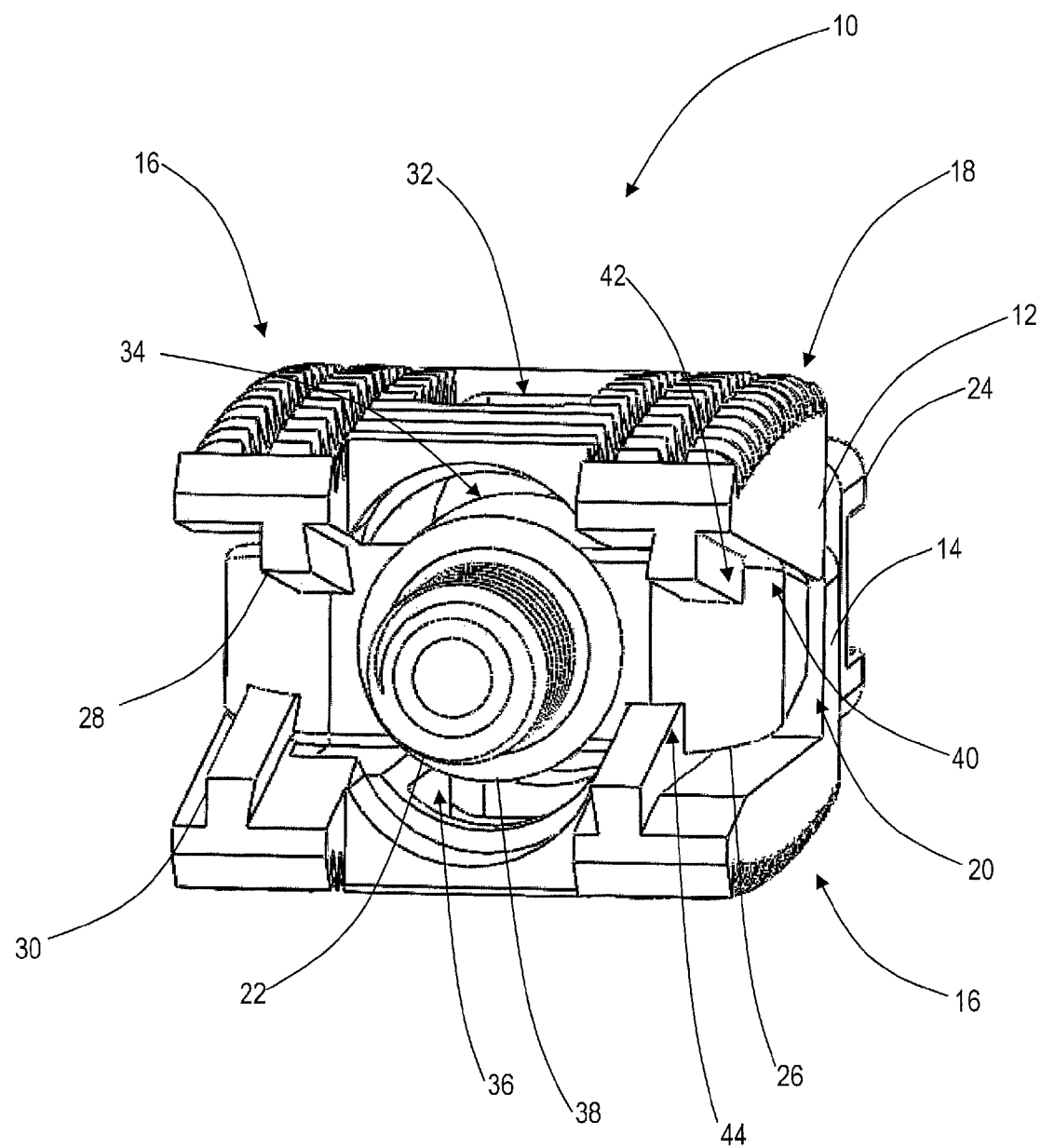
FIG. 3 is a further perspective view of one exemplary embodiment of the expandable intervertebral implant of the present invention.

Another view of the expandable intervertebral implant 10 is provided in FIGS. 2 and 3. As is evident from FIGS. 2 and 3, the superior member 12 and the inferior member 14 may each include one or more holes 32 or fenestrations to promote bony in-growth and fusion, as appropriate. Preferably, the superior member 12 and the inferior member 14 each include a groove 34 and 36 in which the screw 22 is disposed. This nesting of the screw 22 within the superior member 12 and the inferior member 14 provides the expandable intervertebral implant 10 with the smallest possible form factor when undeployed, allowing the superior member 12 and the inferior member 14 to collapse together, without interference from the screw 22. The wedge structure 26 has a corresponding bore portion 38 (FIG. 3), through which the screw 22 passes and which sits within the grooves 34 and 36 of the superior member 12 and the inferior member 14, respectively. This configuration permits the wedge structure 26 to translate smoothly along the central axis of the expandable intervertebral implant 10 with rotation of the screw 22, distracting the superior member 12 and the inferior member 14, which holding the entire assembly in secure alignment. Along these same lines, the cut-away sections 18 and 20 of the superior member 12 and the inferior member 14, respectively, may form abutting surfaces 40 perpendicular to the central axis of the expandable intervertebral implant 10 that aide in holding the superior member 12 and the inferior member 14 in alignment, despite their degree of deployment, by resisting rotation of the superior member 12 and the inferior member 14 with respect to one another. Thus, the expandable intervertebral implant 10 will expand upon deployment, as opposed to "clamshelling." Also along these same lines, the track structures 28 and 30 of the superior member 12 and the inferior member 14 are "dove-tailed" on one or both sides and engage corresponding channels 42 and 44 manufactured into the superior and inferior surfaces of the wedge structure 26, again thereby securely coupling the superior member 12 to the inferior member 14 through the wedge structure 26.

Figure 4:
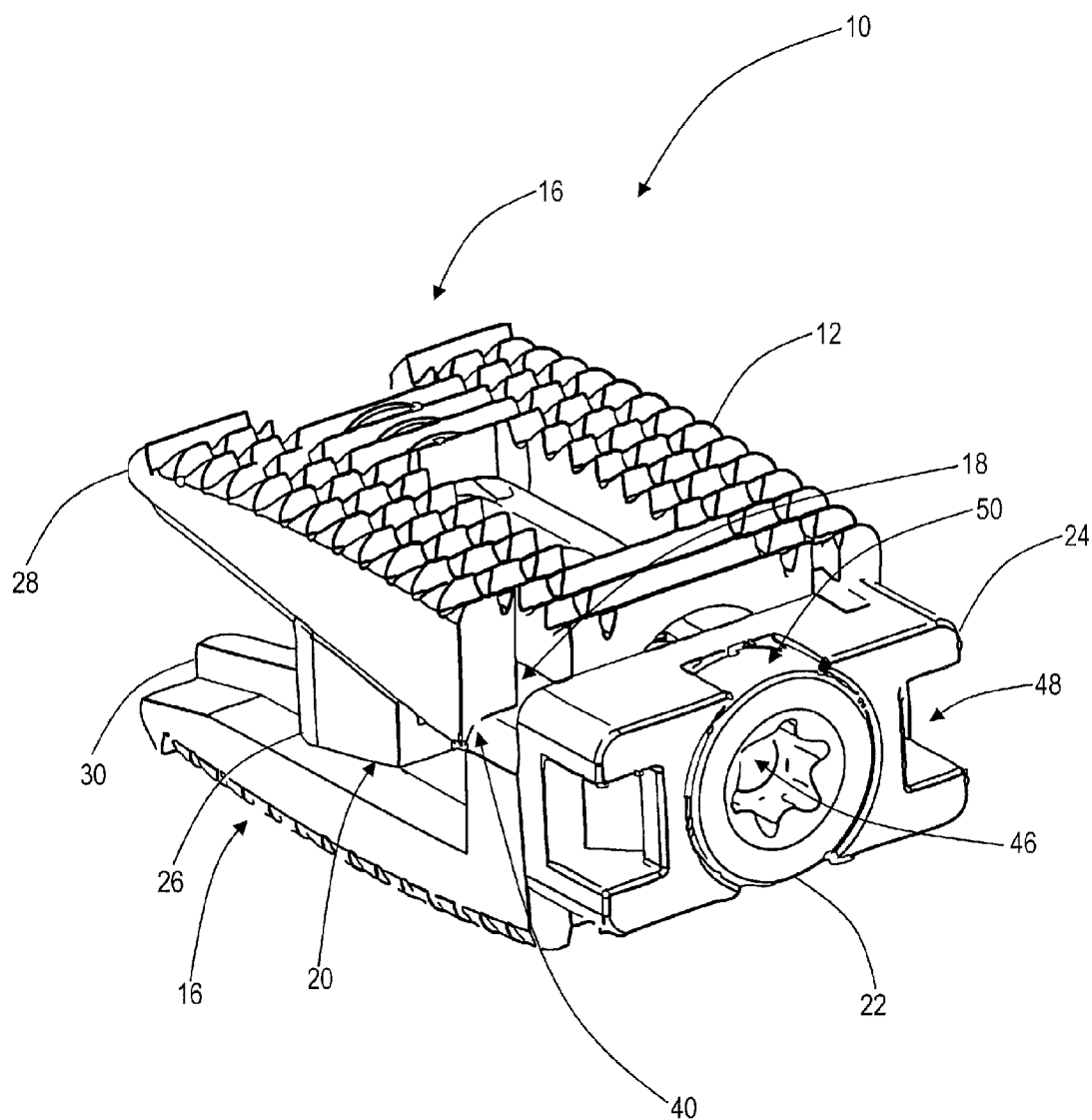
FIG. 4 is a still further perspective view of one exemplary embodiment of the expandable intervertebral implant of the present invention.

Referring to FIG. 4, the screw 22 preferably includes a keyed recess 46 for receiving a driver, such as a hexalobular driver, by which the screw 22 is rotated to translate the wedge structure 26. The housing 24 includes a plurality of recesses 48 or the like for receiving a holding/placement tool. As is described in greater detail herein below, the driver and holding/placement tool may be incorporated into one assembly, such that the expandable intervertebral implant 10 may be grasped, positioned, expanded, and released in a series of simple steps, by a single surgeon, using a single tool. As is also illustrated in FIG. 4, the housing 24 may include a cylindrical recess 50 that is configured to substantially contain the head of the screw 22, again reducing the overall footprint of the expandable intervertebral implant 10.

Figure 5:
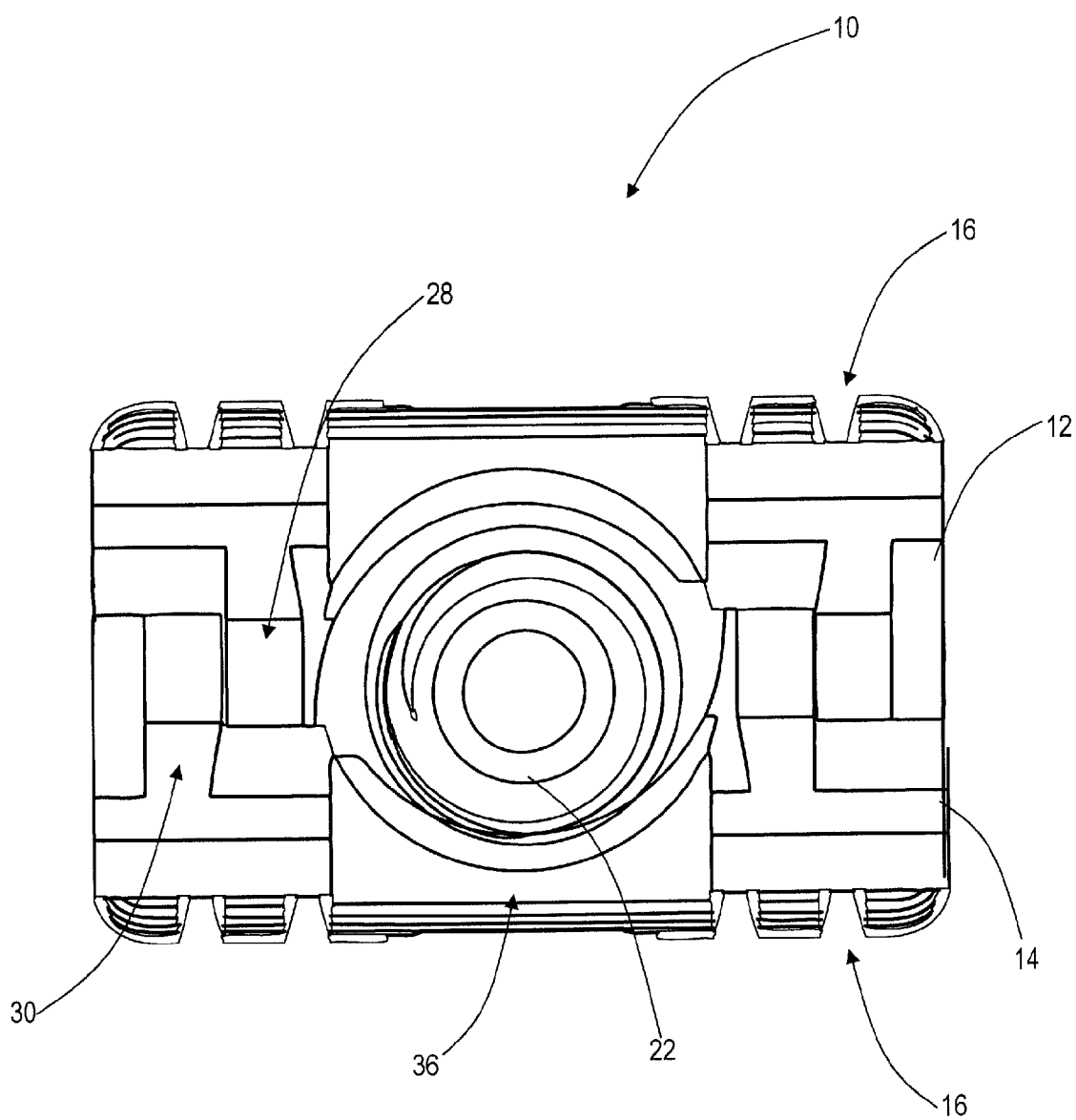
FIG. 5 is a planar end view of one exemplary embodiment of the expandable intervertebral implant of the present invention.
Figure 6:
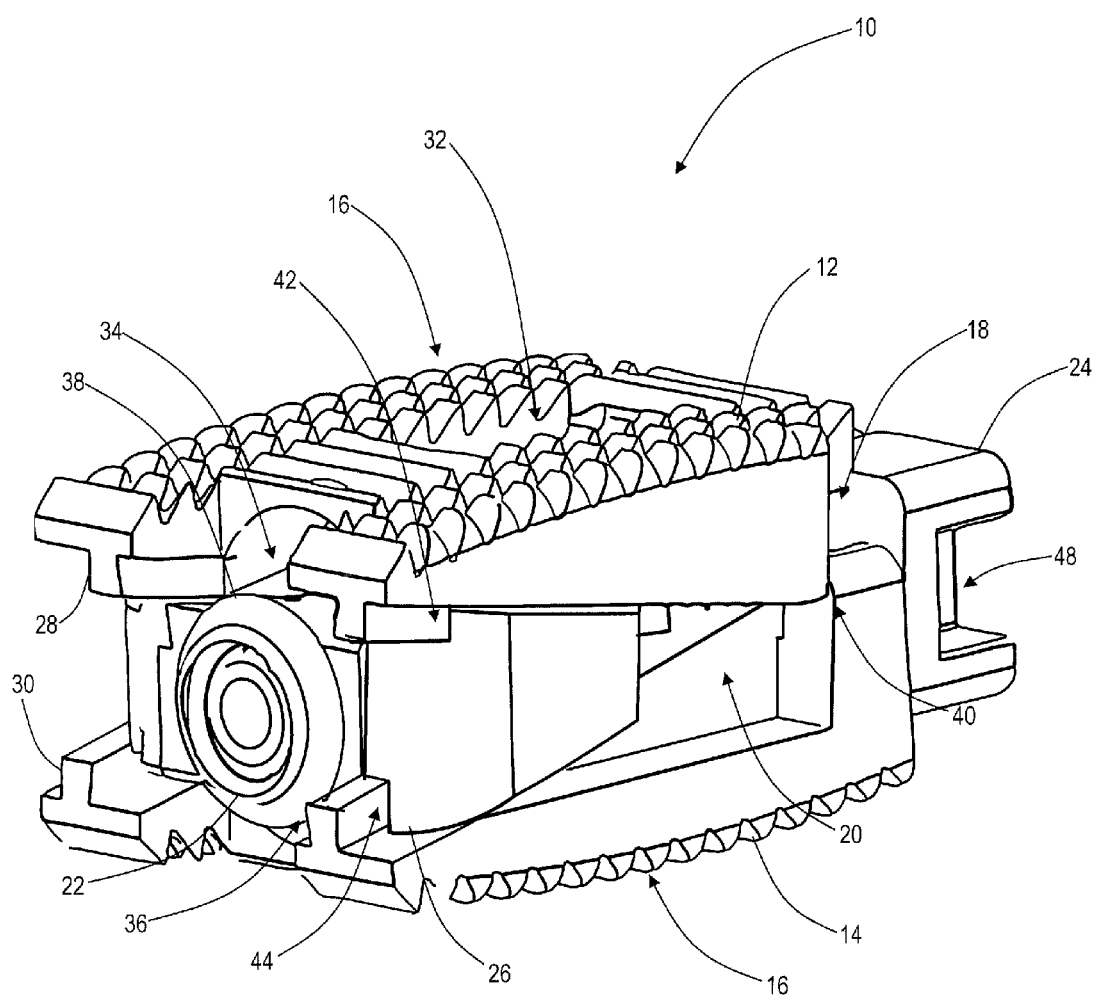
FIG. 6 is a still further perspective view of one exemplary embodiment of the expandable intervertebral implant of the present invention.
Figure 7:
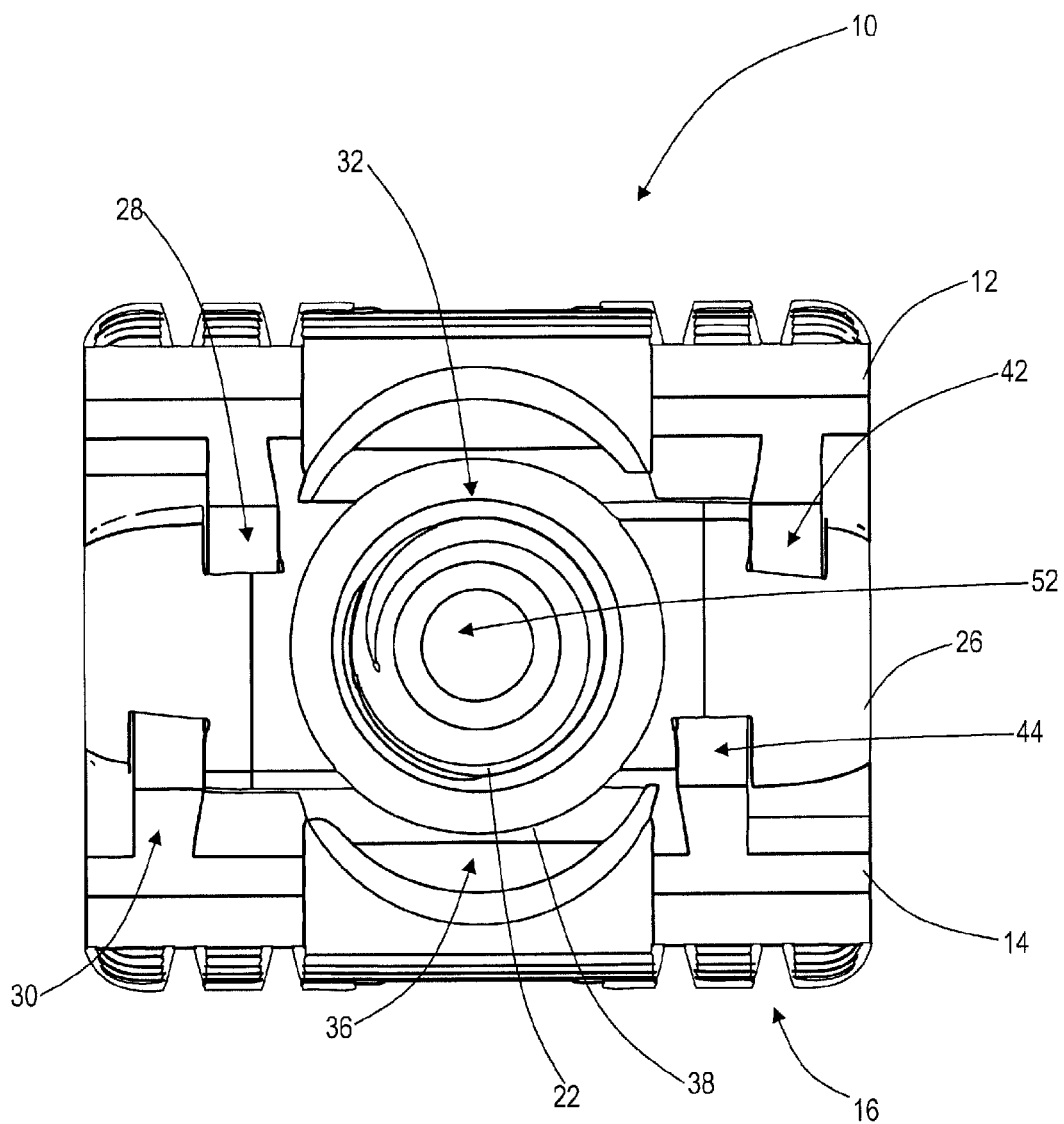
FIG. 7 is another planar end view of one exemplary embodiment of the expandable intervertebral implant of the present invention.

FIG. 5 illustrates the cross-sectional footprint of the expandable intervertebral implant 10 along its central axis, demonstrating how the superior member 12 and the inferior member 14 nest with one another about the screw 22 during implantation. FIG. 6 illustrates the expandable intervertebral implant 10 in an only partially-deployed state, while FIG. 7 illustrates the cross-sectional footprint of the expandable intervertebral implant 10 along its central axis, demonstrating how the superior member 12 and the inferior member 14 expand away from one another about the screw 22 and wedge structure 26 during actuation and deployment. As is illustrated clearly in FIGS. 5 and 7, the screw 22 may be cannulated, and a have a bore 52 passing through it along the central axis of the expandable intervertebral implant 10. This cannulation aides in the placement of the expandable intervertebral implant 10 over a guide-wire or the like.

Figure 8:
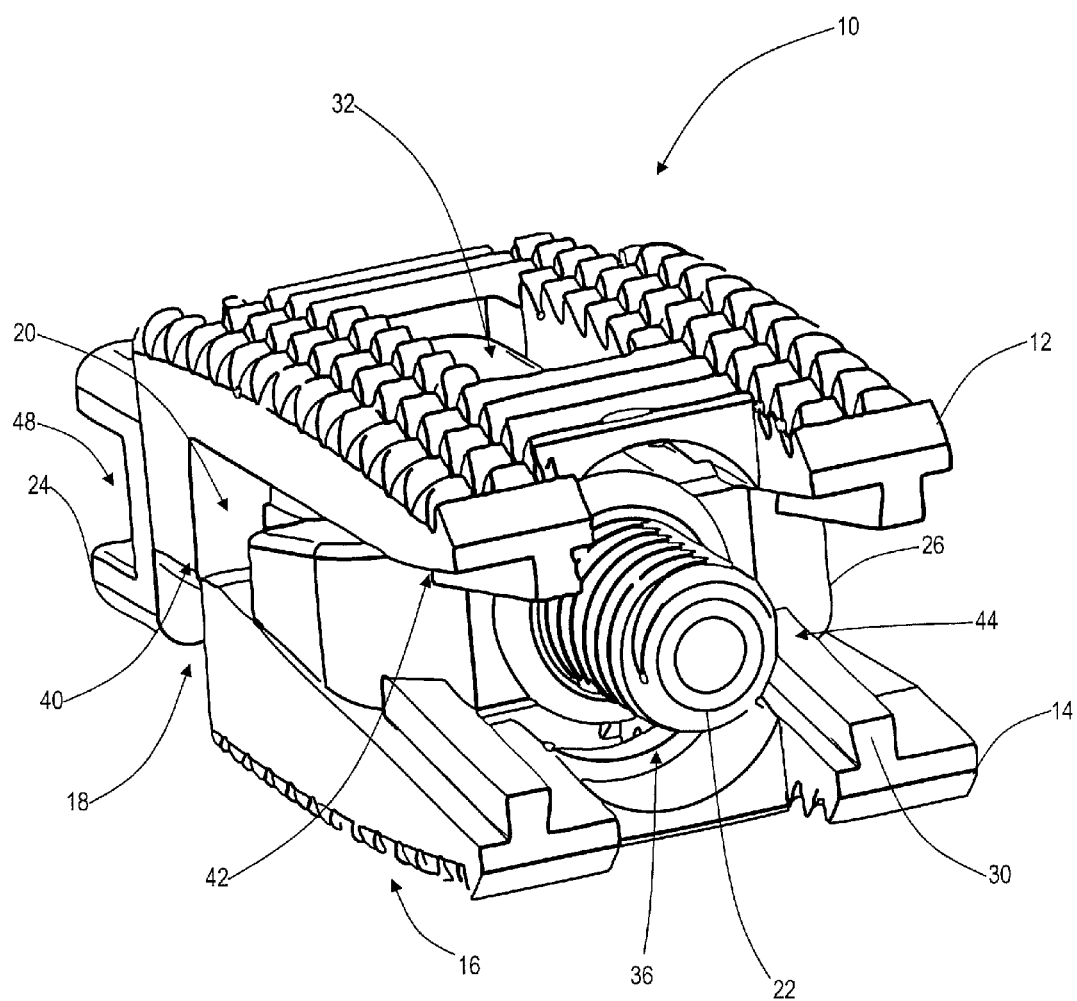
FIG. 8 is a still further perspective view of one exemplary embodiment of the expandable intervertebral implant of the present invention.

Referring to FIG. 8, it may be seen that the track structures 28 and 30 of the superior member 12 and the inferior member 14, respectively, are offset (i.e. staggered) from one another relative to the central axis of the expandable intervertebral implant 10 such that they sit side-by-side when the expandable intervertebral implant 10 is un-depolyed, thereby making the assembly as compact as possible. This also allows the track structures 28 and 30 of the superior member 12 and the inferior member 14 to be longer (versus vertically aligned tracks 28 and 30), thereby permitting the wedge structure 26 of a fully contracted (i.e. fully unexpanded) implant 10 to be disposed within the horizontal footprint of the superior member 12 and the inferior member 14 while maintaining minimum wedge translation (i.e. travel) length requirements to effect the required distraction of the implant 10. Again, this makes the assembly as compact as possible, with the smallest possible undeployed vertical cross-section and the smallest/shortest possible undeployed horizontal footprint. Accordingly, the channels 42 and 44 manufactured into the superior and inferior surfaces of the wedge structure 26, respectively, are also offset from one another relative to the central axis of the expandable intervertebral implant 10. FIG. 8 also illustrates the interaction of the slopes of the wedge structure 26 and, in this exemplary embodiment, the superior member 12. Again, the interaction of the wedge structure 26 with the wedge shape or structure of the superior member 12 and/or inferior member 14 during translation preferably causes the superior member 12 and the inferior member 14 to move apart/together while maintaining a substantially parallel relationship.

Figure 9A:
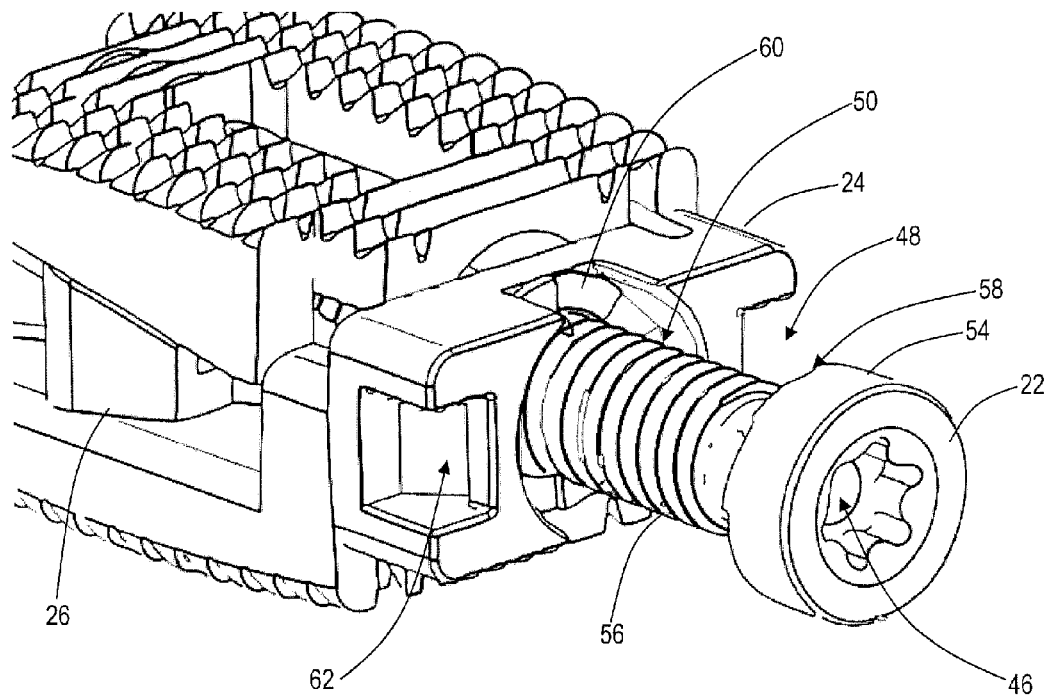
FIG. 9a is a partial perspective view of one exemplary embodiment of the expandable intervertebral implant of the present invention.
Figure 9B:
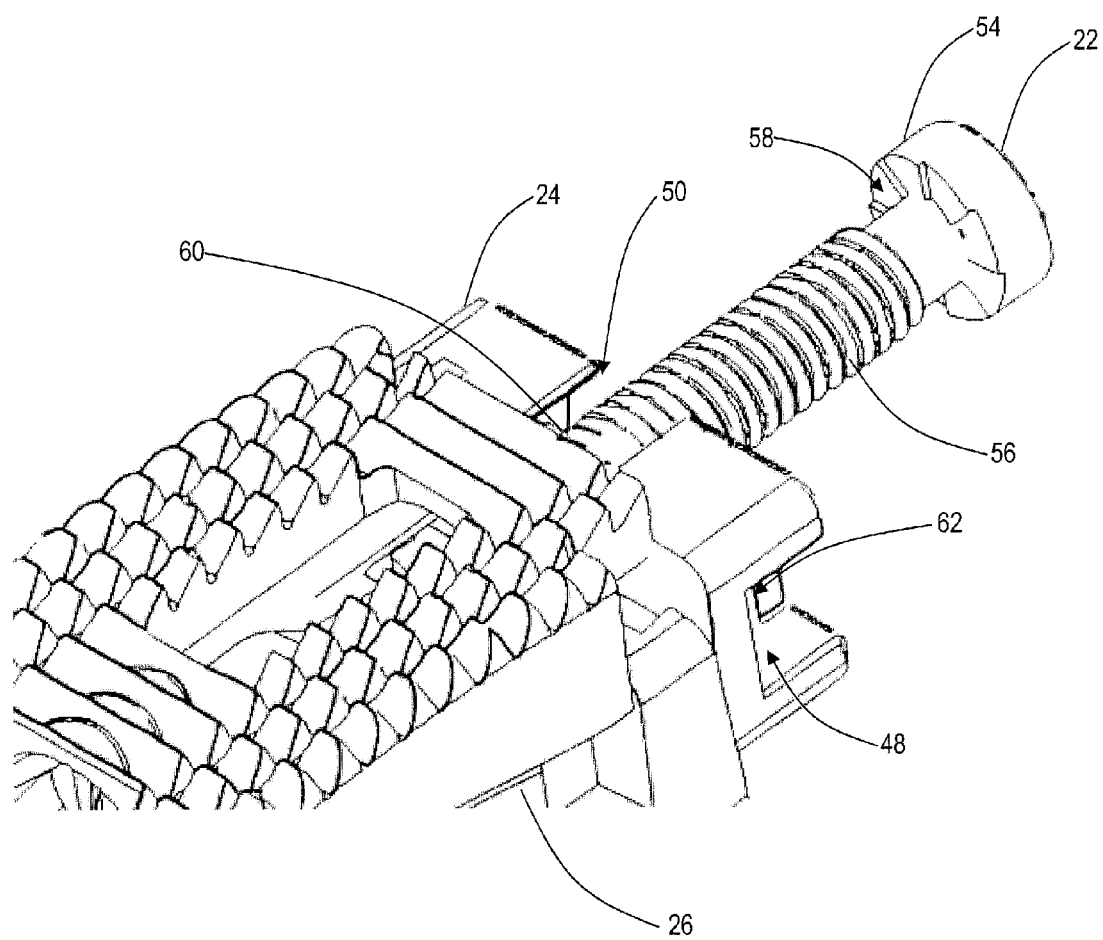
FIG. 9b is another partial perspective view of one exemplary embodiment of the expandable intervertebral implant of the present invention.
Figure 10A:
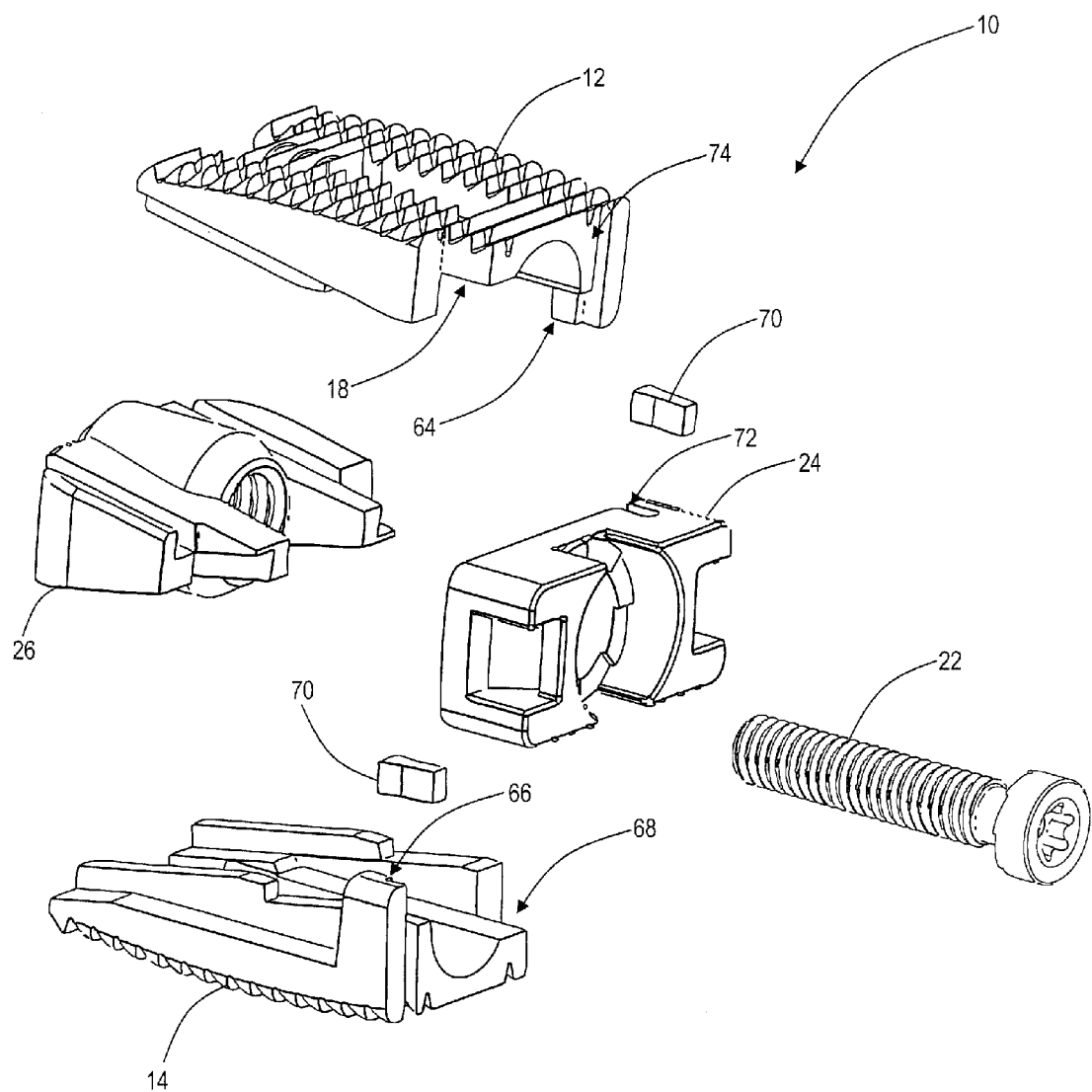
FIG. 10a is an exploded perspective view of one exemplary embodiment of the expandable intervertebral implant of the present invention.
Figure 10B:
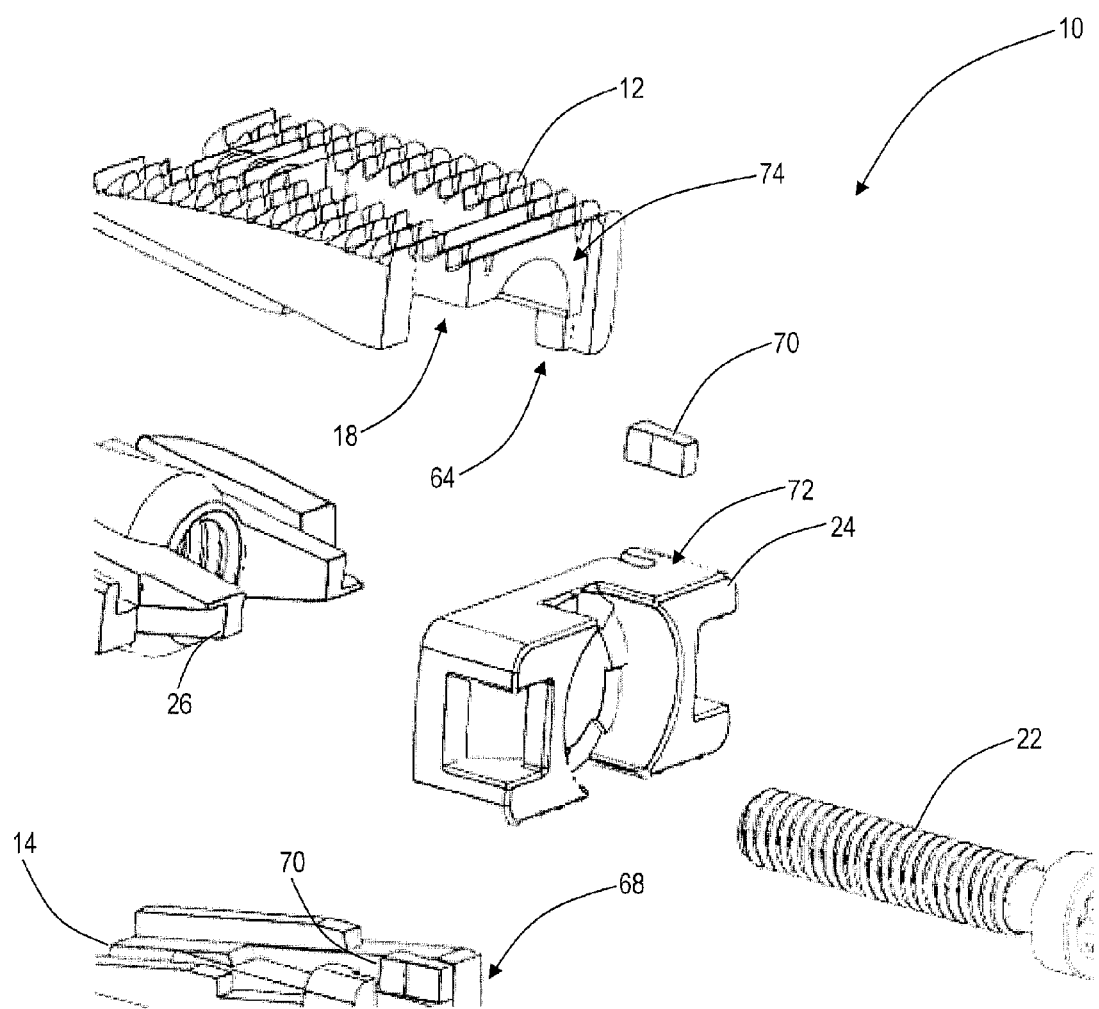
FIG. 10b is a partial exploded perspective view of one exemplary embodiment of the expandable intervertebral implant of the present invention.
Figure 10C:
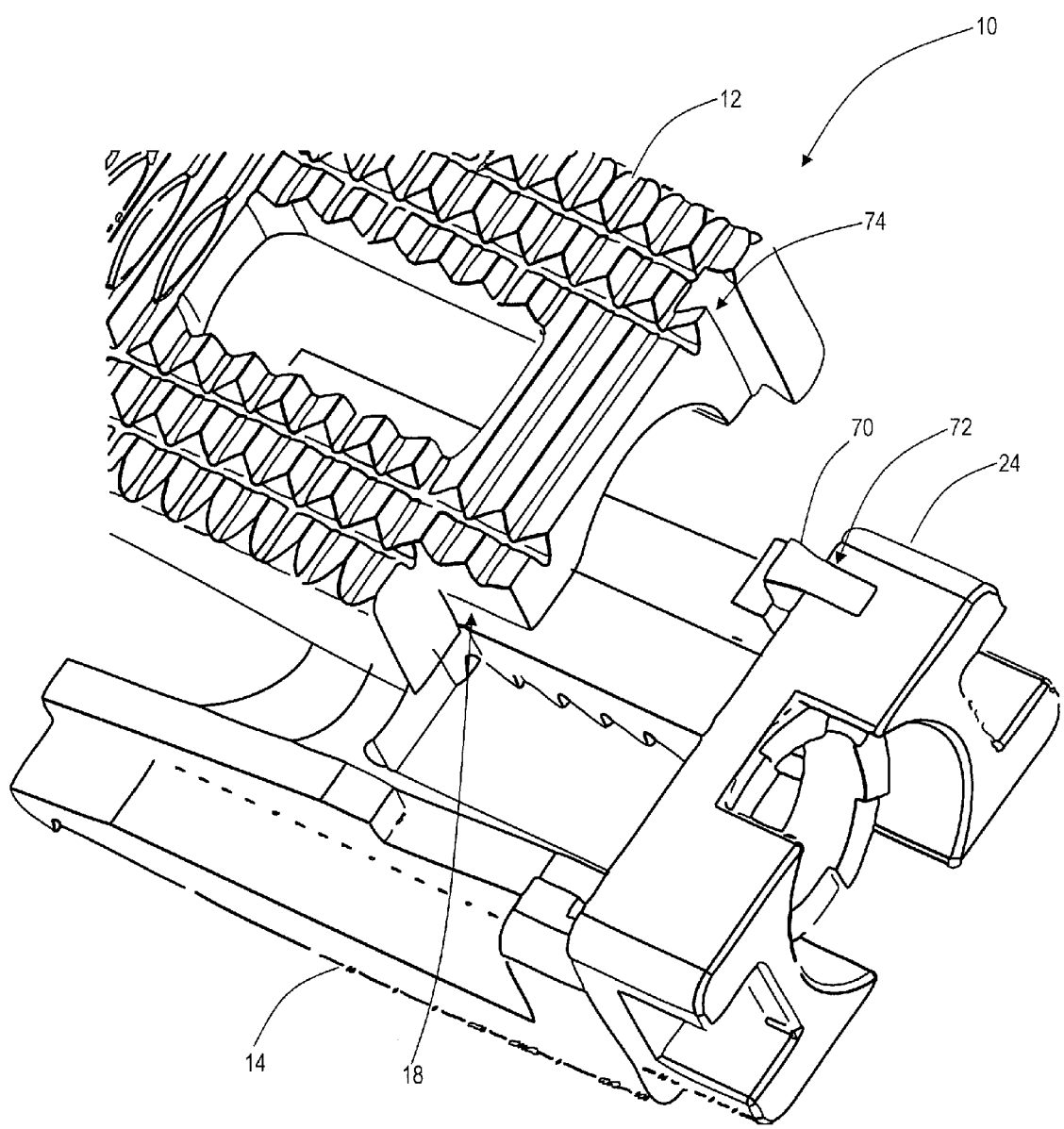
FIG. 10c is another partial exploded perspective view of one exemplary embodiment of the expandable intervertebral implant of the present invention.
Figure 10D:
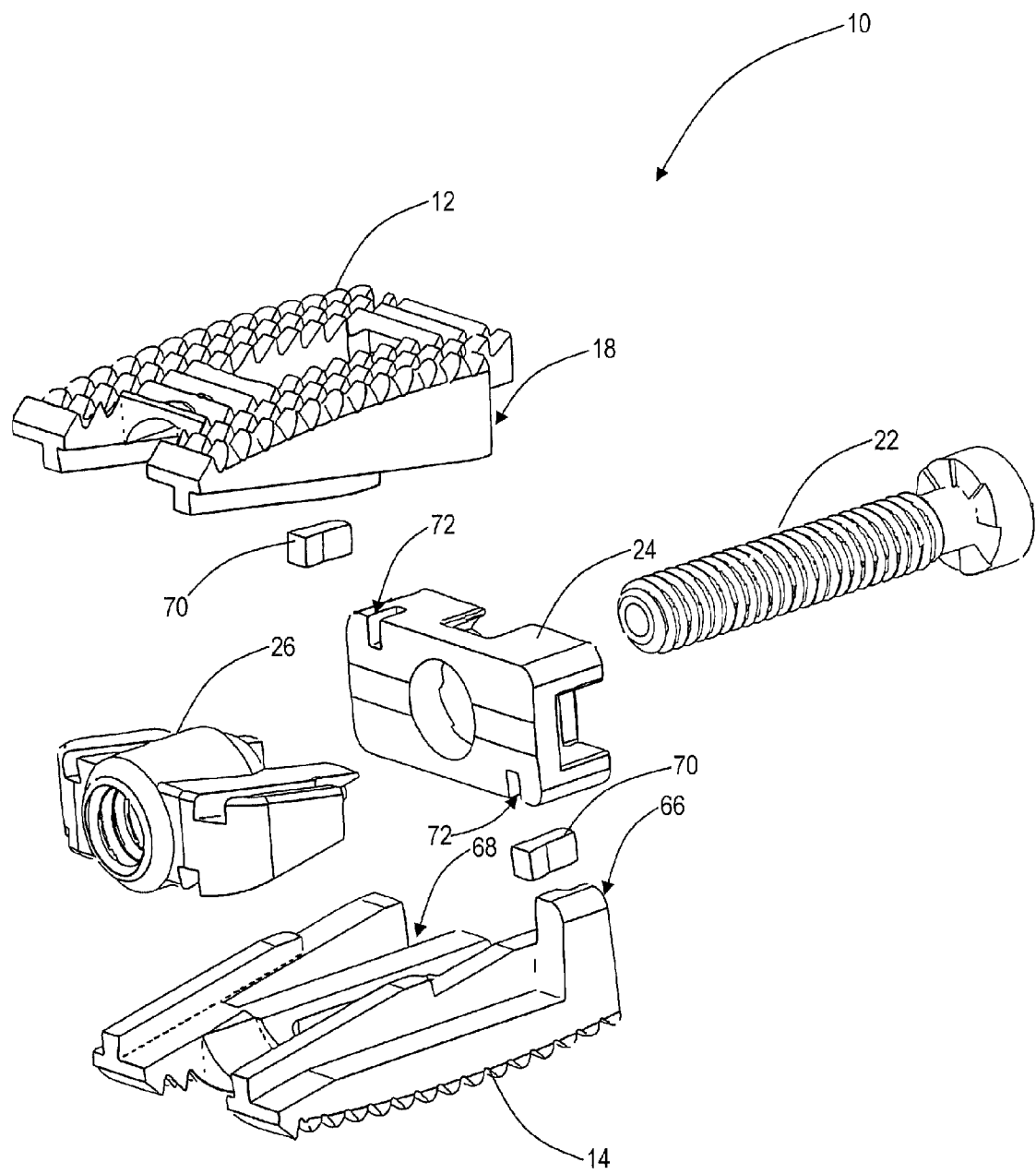
FIG. 10d is another exploded perspective view of one exemplary embodiment of the expandable intervertebral implant of the present invention.
Figure 10E:
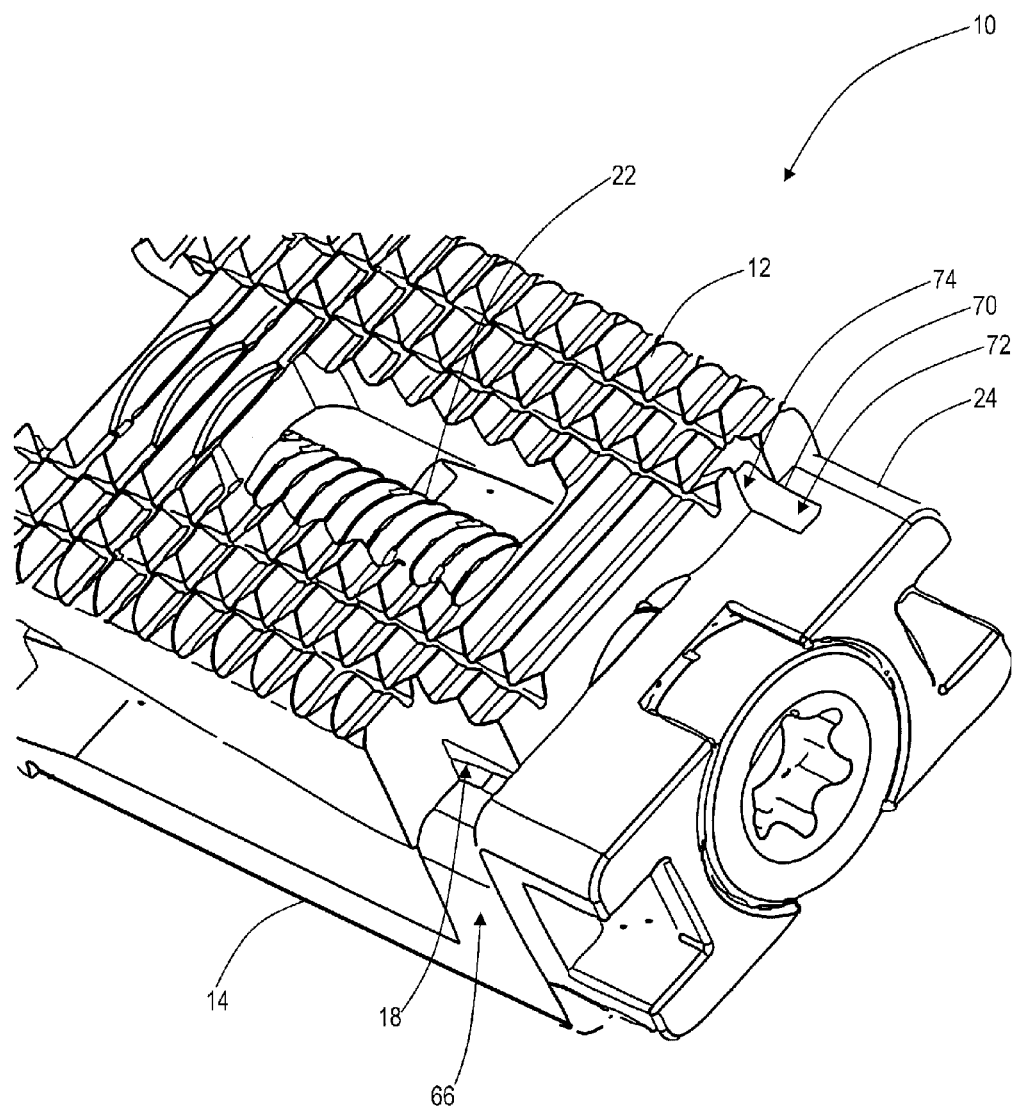
FIG. 10e is a further partial exploded perspective view of one exemplary embodiment of the expandable intervertebral implant of the present invention.

Referring to FIGS. 9*a* and 9*b*, the screw 22 includes a head portion 54 that selectively sits within the cylindrical recess 50 of the housing 24 and a threaded portion 56 that passes through the housing 24 to engage the wedge structure 26. When properly positioned, the head portion 54 of the screw 22 sits flush with the exterior surface of the expandable intervertebral implant 10 and does not protrude. Preferably, the back side of the head portion 54 of the screw 22 includes a plurality of teeth 58 or the like that frictionally engage the screw 22 with a corresponding plurality of teeth 60 or the like manufactured into the exposed floor of the cylindrical recess 50 of the housing 24. This ratcheting or spiral jaw clutch mechanism aides in preventing unwanted rotation of the screw 22 and corresponding translation of the wedge structure 26. This may also aide in allowing the screw 22 to be rotated in a ratcheting or step-wise manner, with specific detent points. It should be noted that a lock-washer or the like could also be used for this purpose, and that a non-screw-based translation assembly could be used to translate and secure the wedge structure 26, as will be readily apparent to those of ordinary skill in the art. Each of the plurality of holding/placement tool recesses 48 includes a lip structure 62 that is selectively engaged by a corresponding hook structure of the tool.

Referring to FIGS. 10*a*-10*e*, the superior member 12 and the inferior member include opposing flanges 64 and 66 that fit within the corresponding cut-away sections 68 and 18 of the inferior member 14 and the superior member 12, respectively, when the superior member 12 and the inferior member 14 are nested against one another and/or separated by a predetermined distance. These opposing flanges 64 and 66 aide in providing stability to the expandable intervertebral implant 10 by preventing the superior member 12 and the inferior member 14 from sliding with respect to one another and the central axis of the expandable intervertebral implant 10. These figures illustrate that the superior member 12 and the inferior member 14 are coupled to one another, but allowed to expand away from/contract towards one another, via a pair of "dove-tailed" inserts 70 or the like disposed on either side of the expandable intervertebral implant 10 that engage both a channel 72 manufactured into the housing 24 and a channel 74 manufactured into the superior member 12 and the inferior member 14. It will be readily apparent to those of ordinary skill in the art that other suitable coupling mechanisms may also be used. In the exemplary embodiment illustrated, only the portion of the inserts 70 engaging the superior member 12 and the inferior member 14 is "dove-tailed," while the portion engaging the housing 24 is not.

Figure 11:
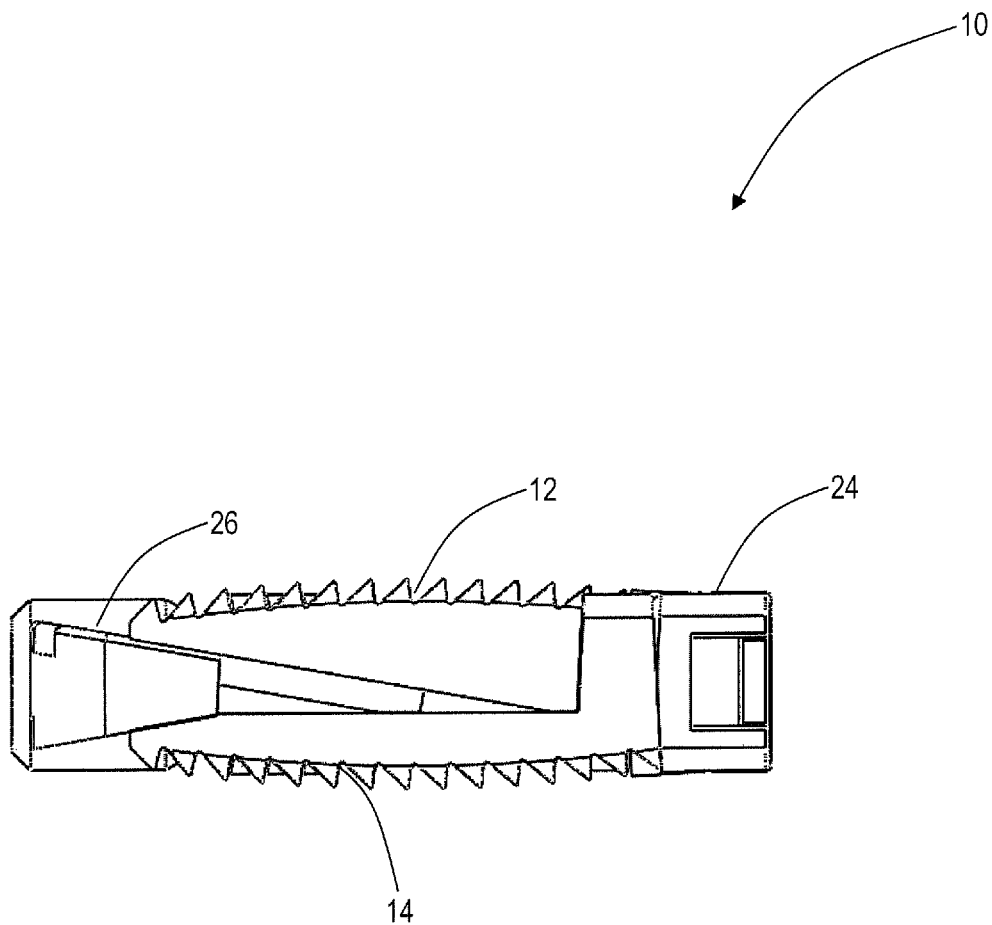
FIG. 11 is a planar side view of one exemplary embodiment of the expandable intervertebral implant of the present invention.
Figure 12:
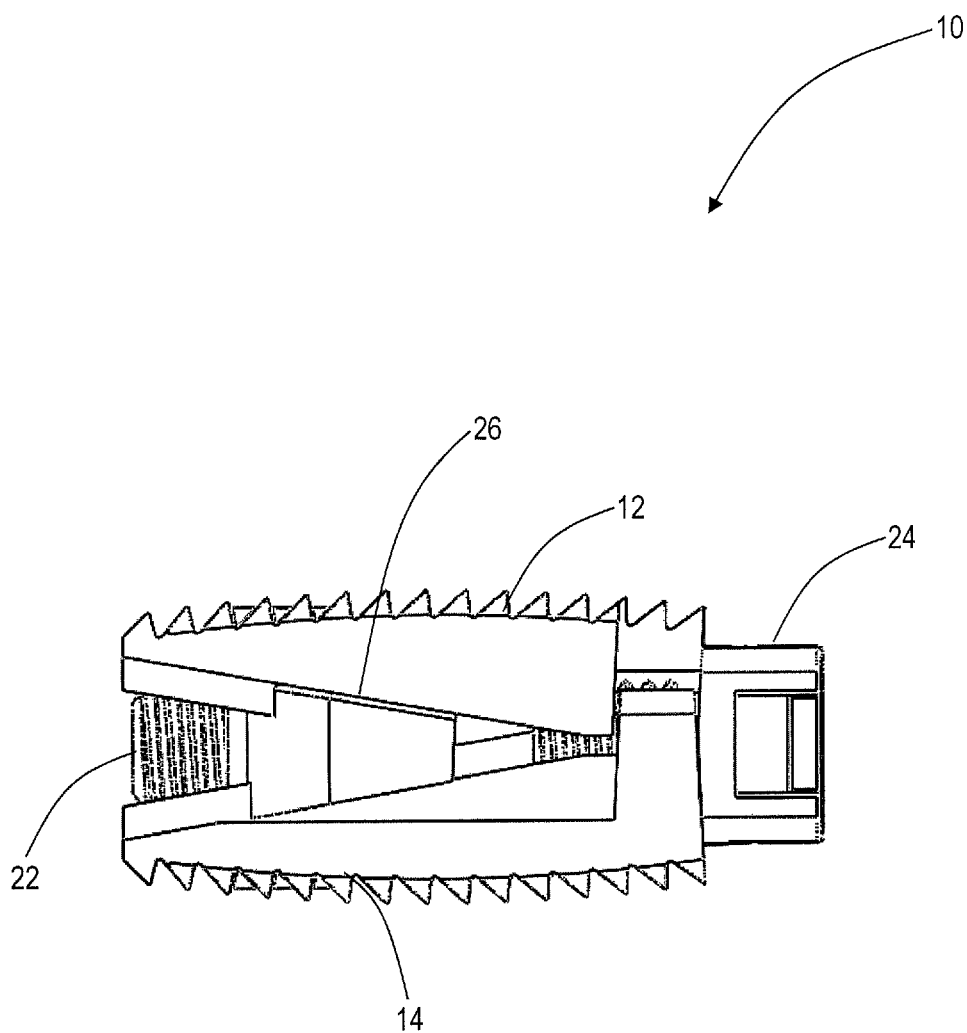
FIG. 12 is another planar side view of one exemplary embodiment of the expandable intervertebral implant of the present invention.
Figure 13:
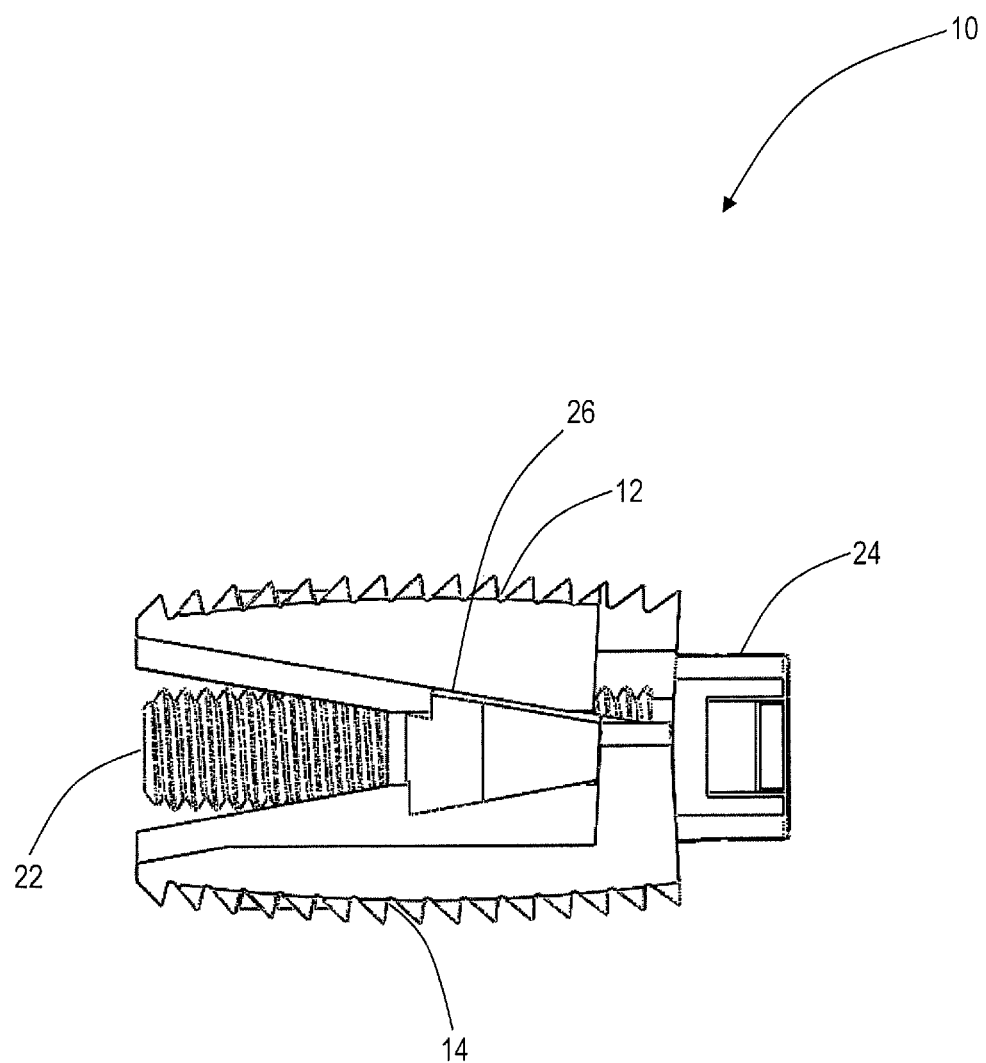
FIG. 13 is a further planar side view of one exemplary embodiment of the expandable intervertebral implant of the present invention.

FIGS. 11-13 illustrate the "opening" of the expandable intervertebral implant 10 via rotation of the screw 22 and translation of the wedge structure 26 towards the housing 24. The constant, substantially-parallel relationship of the superior member 12 and the inferior member 14 should be noted as the wedge structure 26 move along the "rails" of the superior member 12 and the inferior member 14.

Figure 14:
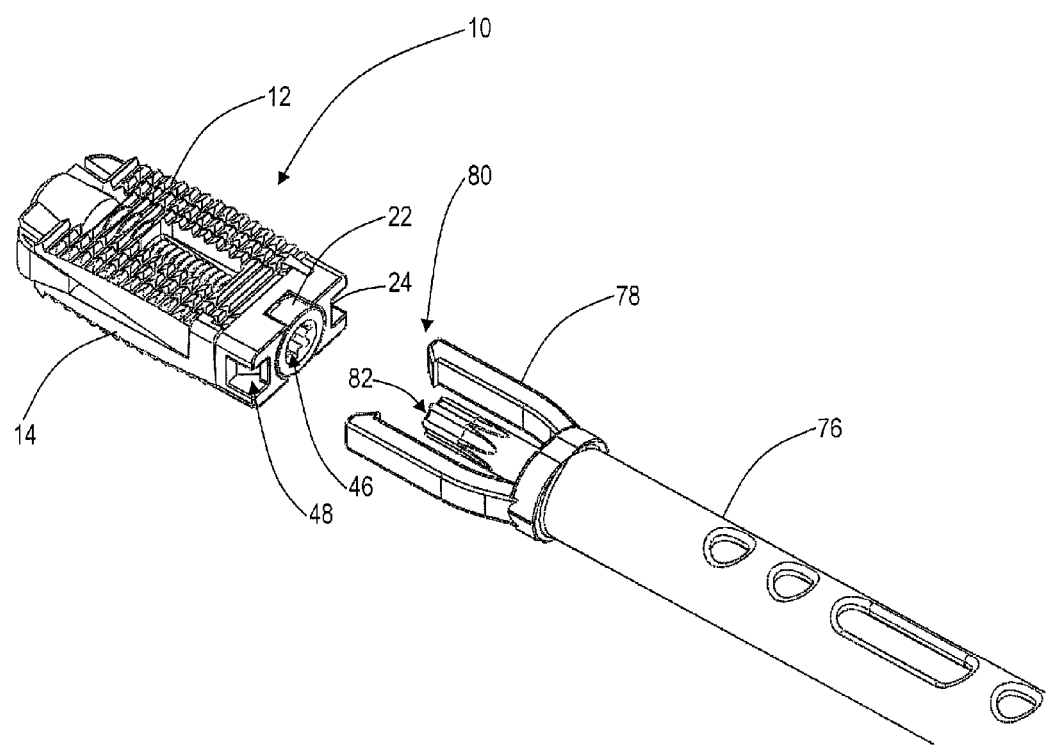
FIG. 14 is a still further perspective view of one exemplary embodiment of the expandable intervertebral implant of the present invention, along with a partial perspective view of one exemplary embodiment of the implantation tool of the present invention.
Figure 15:
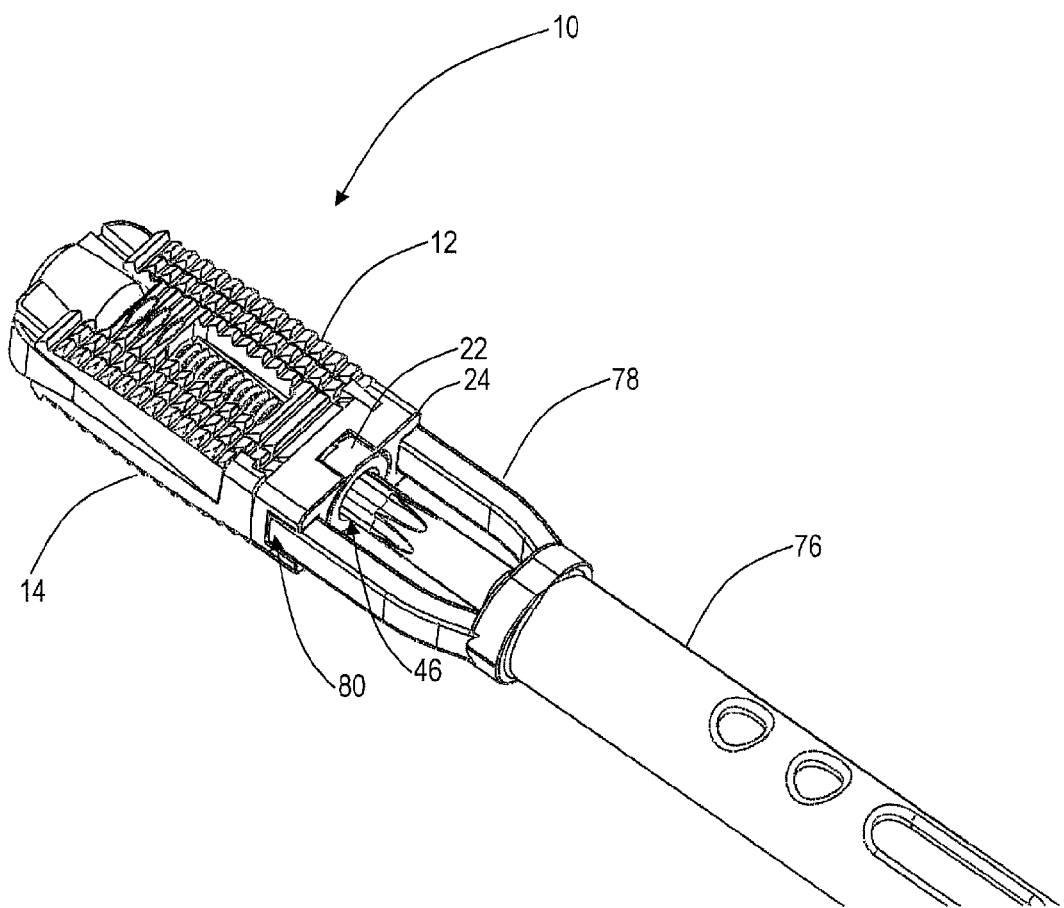
FIG. 15 is a still further perspective view of one exemplary embodiment of the expandable intervertebral implant of the present invention, along with another partial perspective view of one exemplary embodiment of the implantation tool of the present invention.

Referring to FIGS. 14 and 15, in one exemplary embodiment, the combination placement/deployment tool 76 of the present invention includes a pair of elongate arms 78 that each have a hook structure 80 on the end that is configured to selectively and releasably engage the corresponding recess 48 of the housing 24. The combination placement/deployment tool 76 also includes a driver 82 disposed between the pair of elongate arms 78 that is configured to selectively and releasably engage the keyed recess 46 of the screw 22. When rotated, the driver 82 rotates the screw 22, thereby translating the wedge structure 26 (not illustrated) and expanding/contracting the superior member 12 and the inferior member 14 of the expandable intervertebral implant 10.

Figure 16:
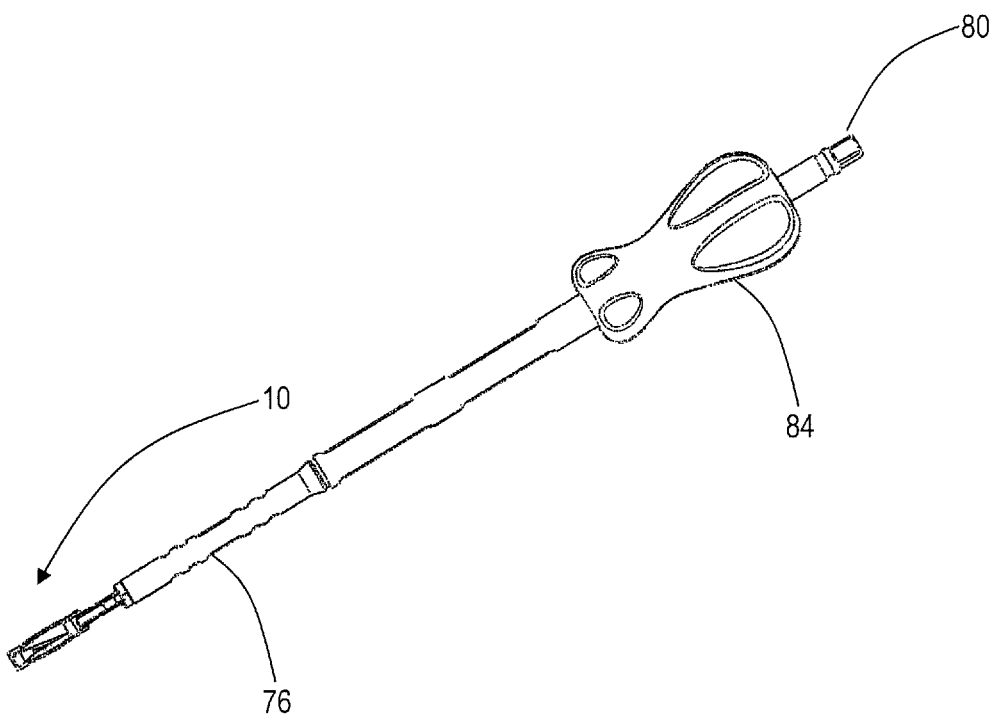
FIG. 16 is a still further perspective view of one exemplary embodiment of the expandable intervertebral implant of the present invention, along with a perspective view of one exemplary embodiment of the implantation tool of the present invention.
Figure 17:
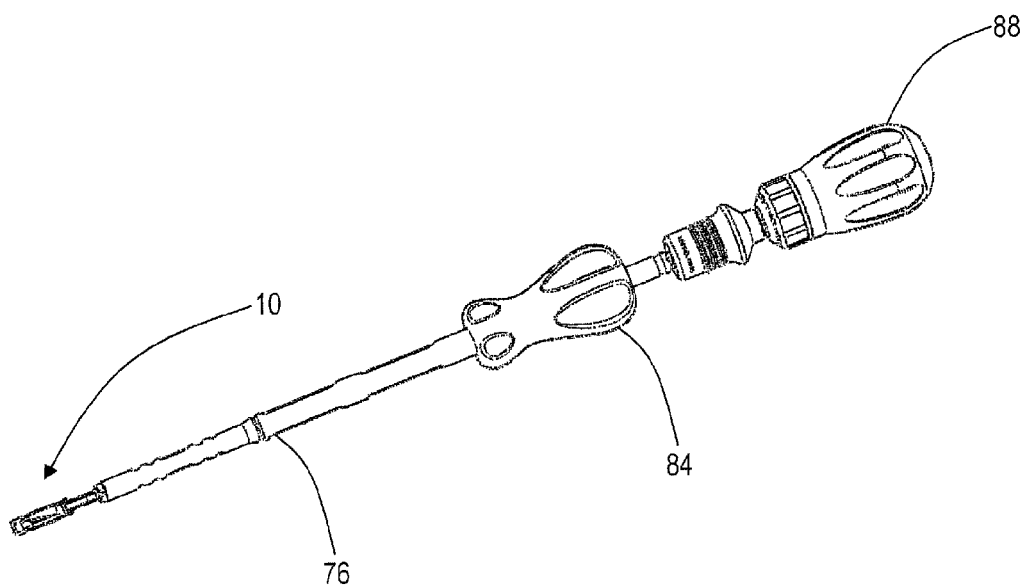
FIG. 17 is a still further perspective view of one exemplary embodiment of the expandable intervertebral implant of the present invention, along with another perspective view of one exemplary embodiment of the implantation tool of the present invention.

Referring to FIGS. 16 and 17, the combination placement/deployment tool 76 further includes a handle 84 for grasping and a socket 86 for attaching a rotating or driver handle 88, such as a ratcheting handle. It will be readily apparent to those of ordinary skill in the art that the expandable intervertebral implant of the present invention may be placed via an open surgical procedure, or via any suitable minimally-invasive portal-type of system.

Figure 18A:
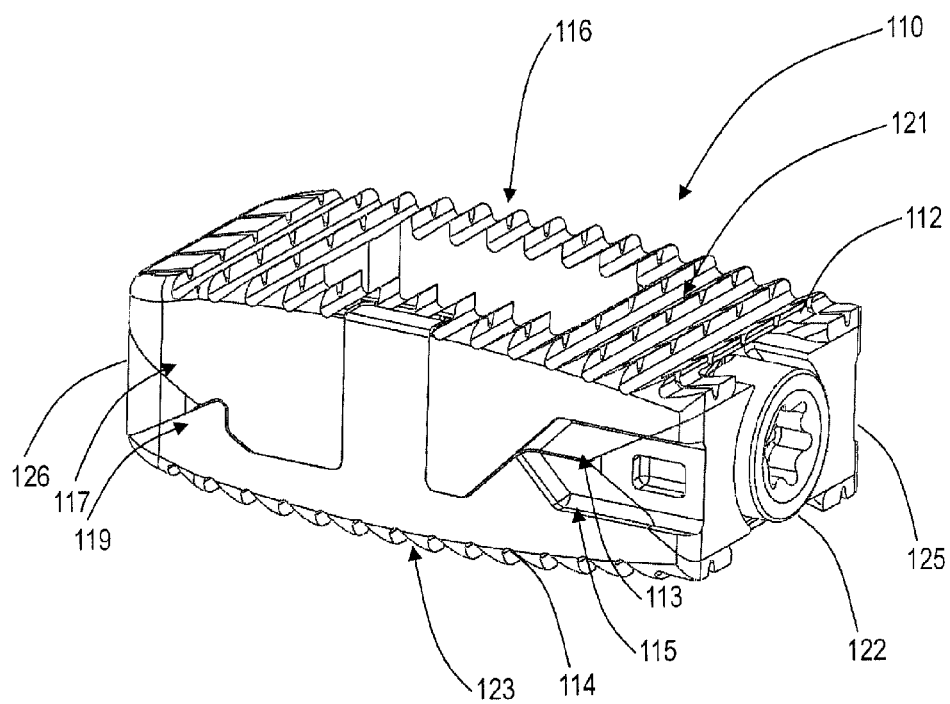
FIGS. 18a and 18b are perspective views of an alternative exemplary embodiment of the expandable intervertebral implant of the present invention in an unexpanded configuration.
Figure 18B:
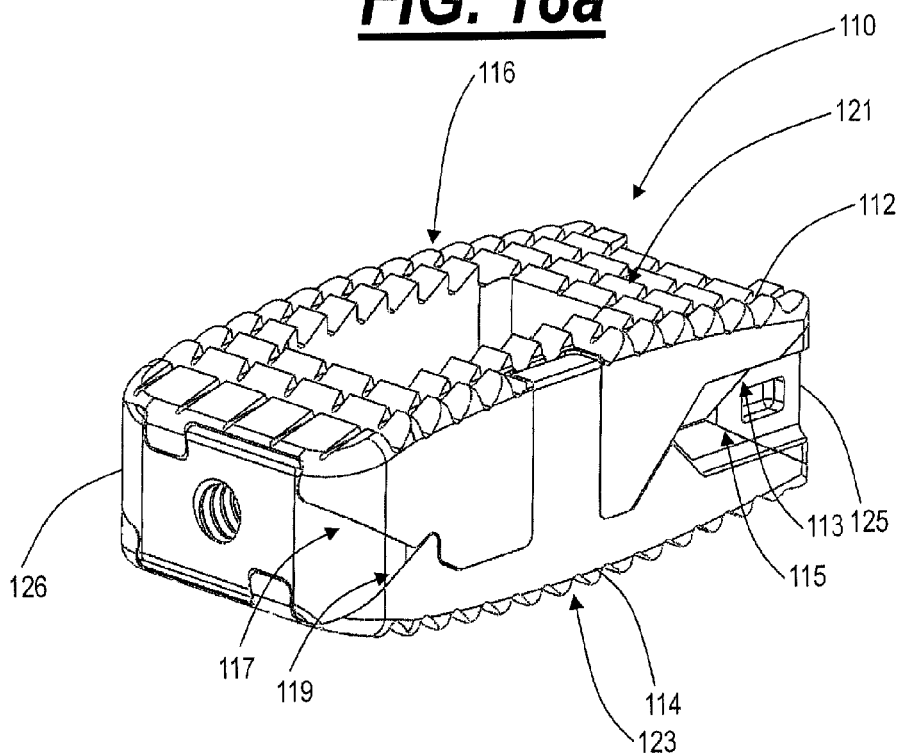
Figure 19A:
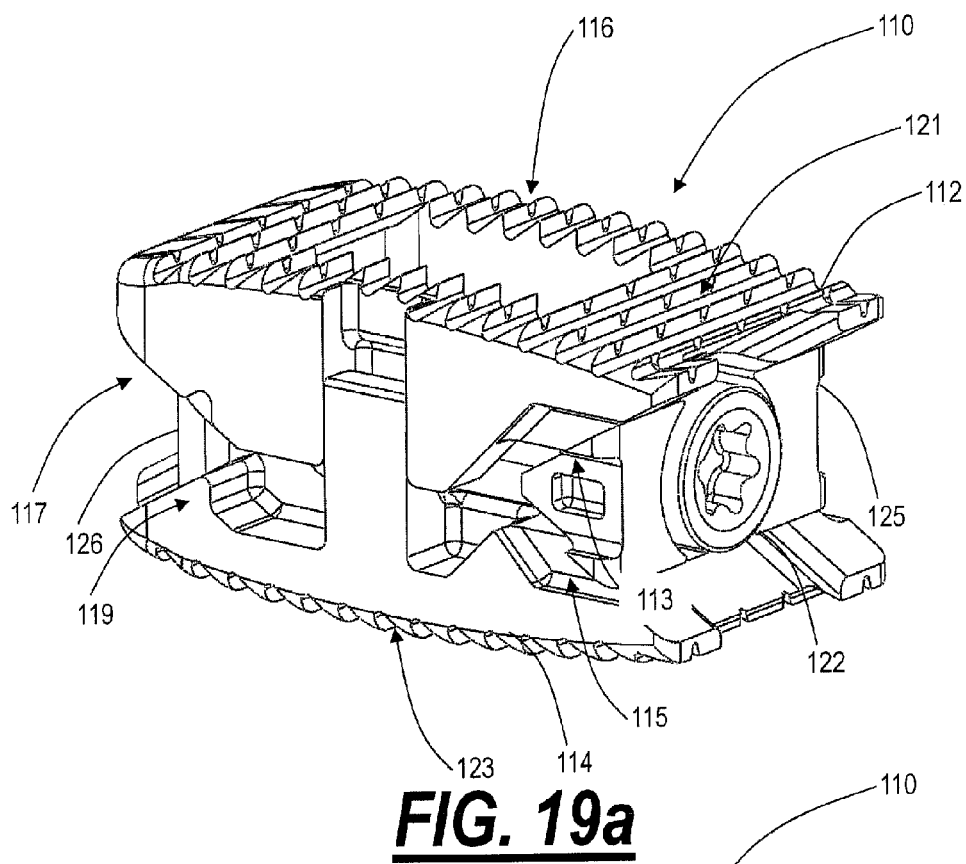
FIGS. 19a and 19b are perspective views of an alternative exemplary embodiment of the expandable intervertebral implant of the present invention in a partially or wholly expanded configuration.
Figure 19B:
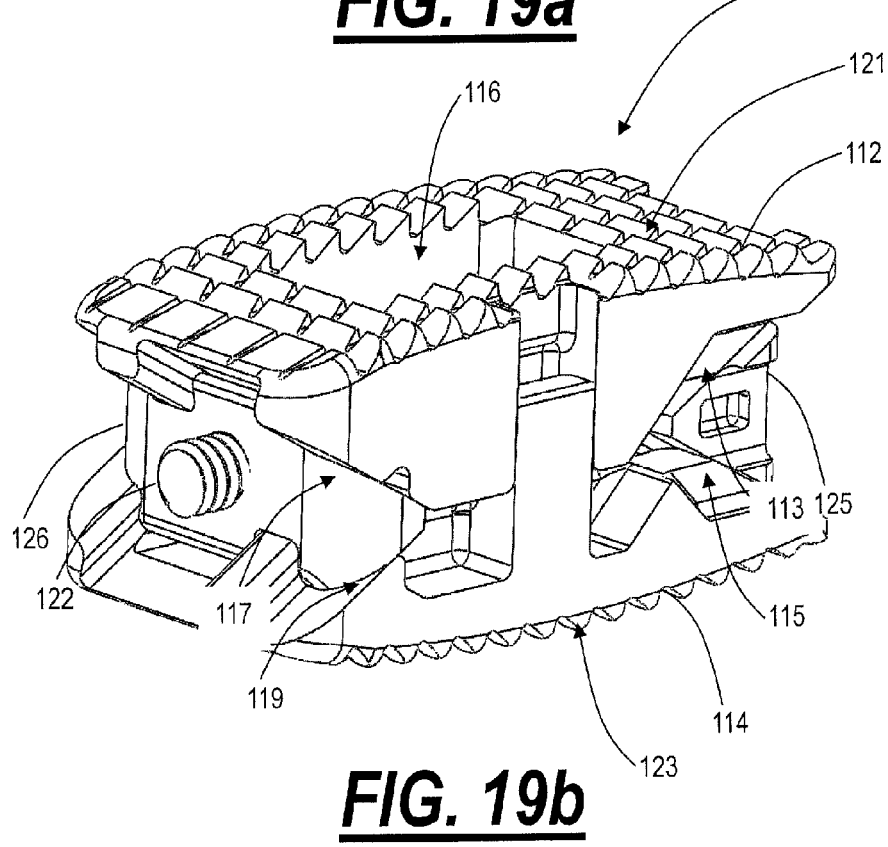

Referring to FIGS. 18*a*, 18*b*, 19*a*, and 19*b*, in an alternative exemplary embodiment, the present invention provides an expandable intervertebral implant 110 that is selectively disposed in the intervertebral space and deployed, thereby in-situ distracting, realigning, and/or stabilizing or fusing a portion of the spine of a patient in the treatment of injury, disease, and/or degenerative condition. FIGS. 18*a* and 18*b* illustrate the expandable intervertebral implant 110 in an unexpanded, or unactuated, configuration, while FIGS. 19*a* and 19*b* illustrate the expandable intervertebral implant 110 in a partially or wholly expanded, or partially or wholly actuated, configuration. The expandable intervertebral implant 110 again includes a superior member 112 and an inferior member 114, each of which has a proximal ramp portion 113 and 115, respectively, and a distal ramp portion 117 and 119, respectively, and a partially or substantially convex or flat opposing surface 121 and 123, respectively, that is suitable for engaging the substantially concave or flat opposing surfaces of the associated bony superior and inferior intervertebral endplates, once properly prepared. Optionally, the superior member 112 and the inferior member 114 are each thinner at the proximal and distal ends of the expandable intervertebral implant 110 than they are in the central portion of the expandable intervertebral implant 110, such that insertion into the intervertebral space may be aided, although this is not a requirement and the expandable intervertebral implant 110 may have a uniform thickness, when undeployed and/or deployed, from the proximal end to the distal end through the central portion. For similar reasons, the proximal and distal ends of the both the superior member 112 and the inferior member 114 may have a narrowed or rounded shape in any dimension or direction. Once disposed in the intervertebral space, the expandable intervertebral implant 110 is actuated and deployed, with the superior member 112 and the inferior member 114 moving apart from one another, while remaining in a substantially parallel and translationally constant configuration, seating against the associated intervertebral endplates, and distracting, realigning, and/or stabilizing them to a desired degree. The mechanisms by which this happens are described in greater detail herein below. This operation is analogous to placing a jack under a car, positioning it appropriately, snugging it in the space beneath the car, and then jacking it up. In order to ensure that the expandable intervertebral implant 110 is held securely in the intervertebral space, the external surface of each of the superior member 112 and the inferior member 114 is provided with a plurality of ridges 116 or other friction structures, providing purchase with the associated intervertebral endplates. The overall dimensions of the expandable intervertebral implant 10 are on the order of several millimeters to tens of millimeters, such that a set of implants containing a series of incremental implant sizes can provide a height expansion range of 7-18 mm or more than 3-5 mm each, for example. Other suitable dimensions may, of course, be utilized.

When undeployed, the superior member 112 and the inferior member 114 are configured such that they nest against and interlock with one another, thereby providing the undeployed expandable intervertebral implant 110 with the smallest possible form factor (i.e. the smallest possible undeployed vertical cross-section and the smallest/shortest possible undeployed horizontal footprint) for insertion through the skin and musculature of the patient and into the intervertebral space. Again, the mechanisms by which this happens are described in greater detail herein below.

By way of overview, the superior member 112 and the inferior member 114 are actuated via the rotation of an actuation bolt 122 disposed through an internally-bored proximal wedge structure 125 that securely, and in a sliding manner, engages the proximal ramp portions 113 and 115 of the superior member 112 and the inferior member 114, respectively, at the proximal end of the expandable intervertebral implant 110. This actuation bolt 122 is disposed along and through the central axis of the expandable intervertebral implant 110, between the superior member 112 and the inferior member 114. At the distal end of the expandable intervertebral implant, the actuation bolt 122 engages an internally-threaded distal wedge structure 126 that securely, and in a sliding manner, engages the distal ramp portions 117 and 119 of the superior member 112 and the inferior member 114, respectively. The proximal and distal wedge structures 125 and 126 are thereby translated along the central axis of the expandable intervertebral implant 110 with rotation of the actuation bolt 122, at least with respect to one another. This translation causes the proximal and distal wedge structures 125 and 126 to interact with the proximal and distal ramp portions 113, 115, 117, and 119 of the superior member 112 and the inferior member 114, thereby forcing the superior member 112 and the inferior member 114 apart/together with translation of the proximal and distal wedge structures 125 and 126. Preferably, the superior member 112 and the inferior member 114 each include a nested track structure (described in greater detail herein below), thereby securely coupling the superior member 112 to the inferior member 114 through the proximal and distal wedge structures 125 and 126. This also allows the track structures of the superior member 112 and the inferior member 114 to be longer (versus vertically aligned tracks), thereby permitting the wedge structures 125 and 126 of a fully contracted (i.e. fully unexpanded) implant 110 to be disposed within the horizontal footprint of the superior member 112 and the inferior member 114 while maintaining minimum wedge translation (i.e. travel) length requirements to effect the required distraction of the implant 110. Again, this makes the assembly as compact as possible, with the smallest possible undeployed vertical cross-section and the smallest/shortest possible undeployed horizontal footprint. The interaction of the proximal and distal wedge structures 125 and 126 with the proximal and distal ramp portions 113, 115, 117, and 119 of the superior member 112 and the inferior member 114 during translation preferably causes the superior member 112 and the inferior member 114 to move apart/together while maintaining a substantially parallel, translationally constant relationship. Alternatively, the superior member 112 and the inferior member 114 may move apart with a predetermined lordotic angle. The superior member 112 and the inferior member 114 may move apart in a substantially continuous fashion, or they may move apart in 0.5-mm or smaller increments, for example. In addition, the interaction of the proximal and distal wedge structures 125 and 126 with the proximal and distal ramp portions 113, 115, 117, and 119 of the superior member 112 and the inferior member 114 may be designed such that as the superior member 112 and the inferior member 114 move apart, they also translate with respect to one another. This is helpful in, for example, ensuring that the plurality of ridges 116 or other friction structures are securely seated in the bony material.

Figure 20:
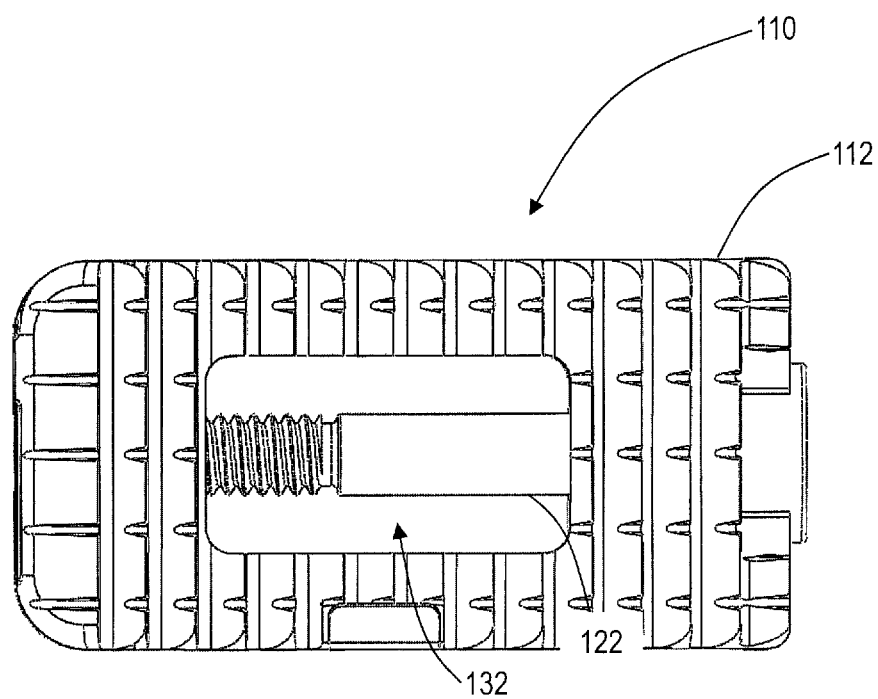
FIG. 20 is a top/bottom planar view of an alternative exemplary embodiment of the expandable intervertebral implant of the present invention.

Another view of the expandable intervertebral implant 110 is provided in FIG. 20. As is evident from FIG. 20, the superior member 112 and the inferior member 114 (not shown here) may each include one or more holes 132 or fenestrations to promote bony in-growth and fusion, as appropriate. For example, the expandable intervertebral implant 110 may include a 40 mm$^2$ or larger axial graft chamber opening or the like for the placement of a fusion material.

Figure 21A:
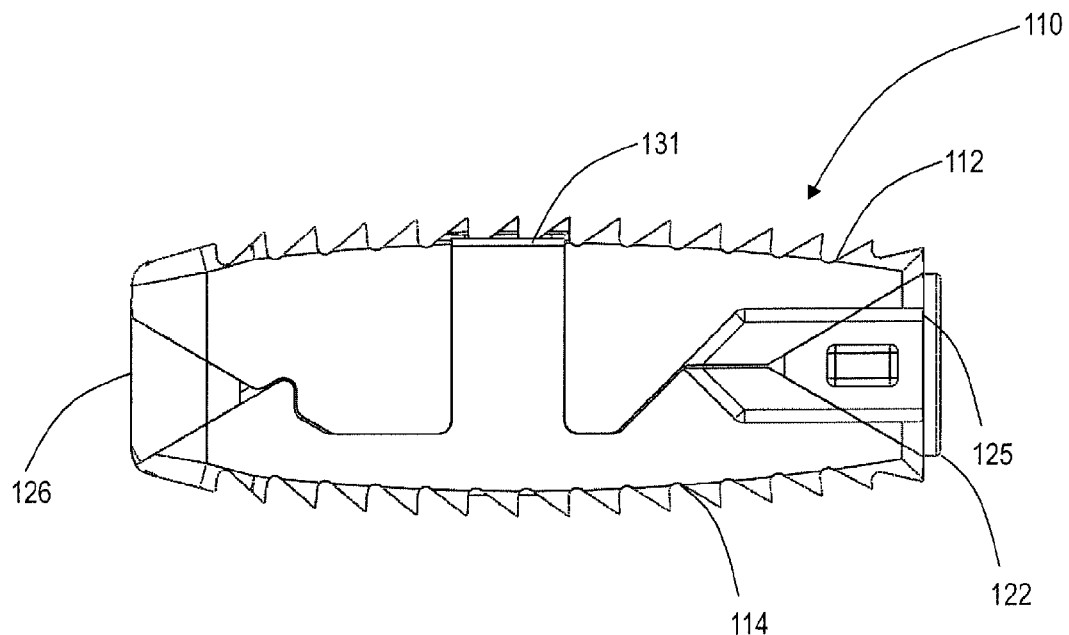
FIGS. 21a and 21b are side planar views of an alternative exemplary embodiment of the expandable intervertebral implant of the present invention in both unexpanded and partially or wholly expanded configurations.
Figure 21B:
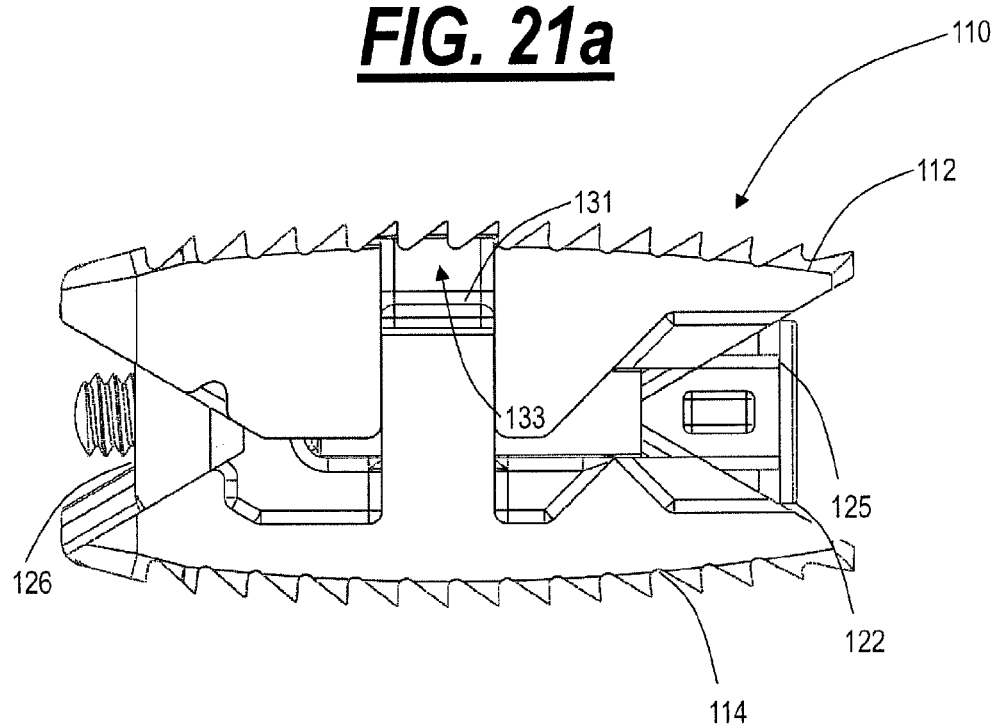
Figure 22A:
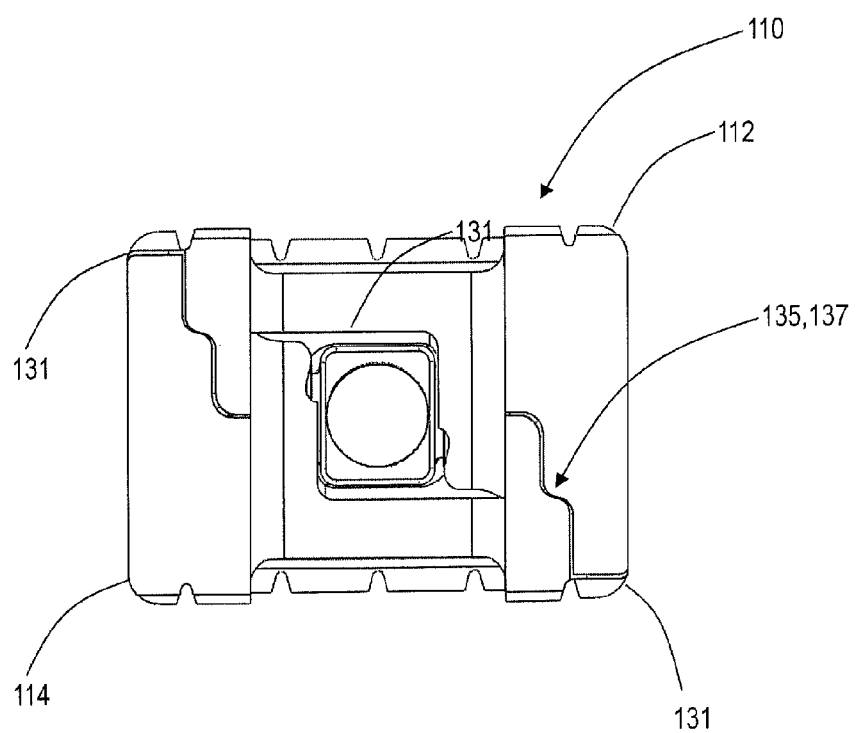
FIGS. 22a and 22b are partial planar views of an alternative exemplary embodiment of the expandable intervertebral implant of the present invention in both unexpanded and partially or wholly expanded configurations.
Figure 22B:
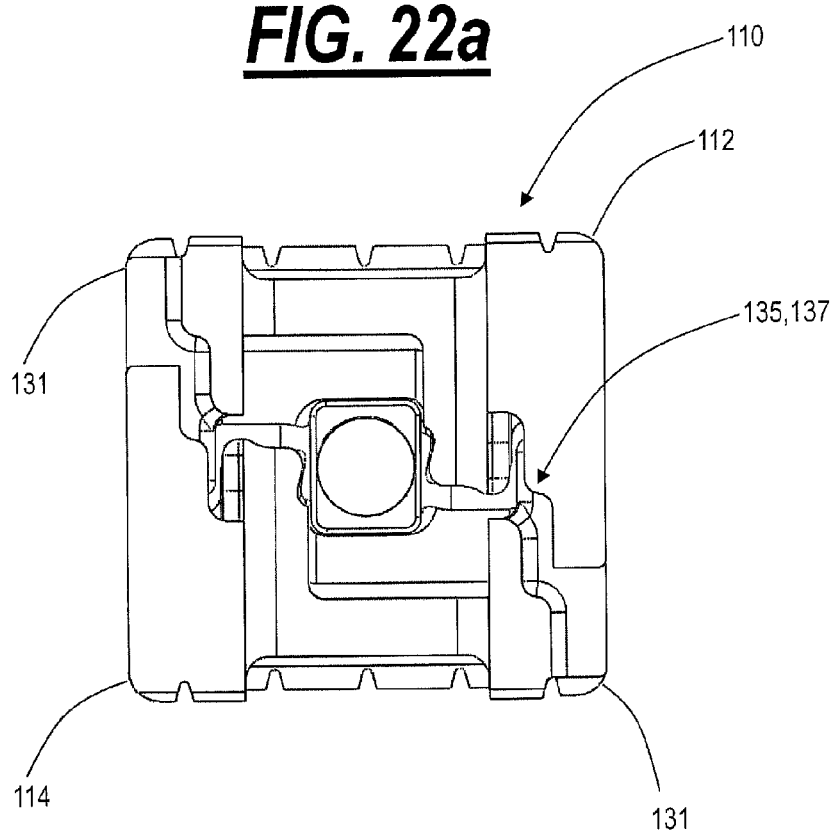
Figure 23A:
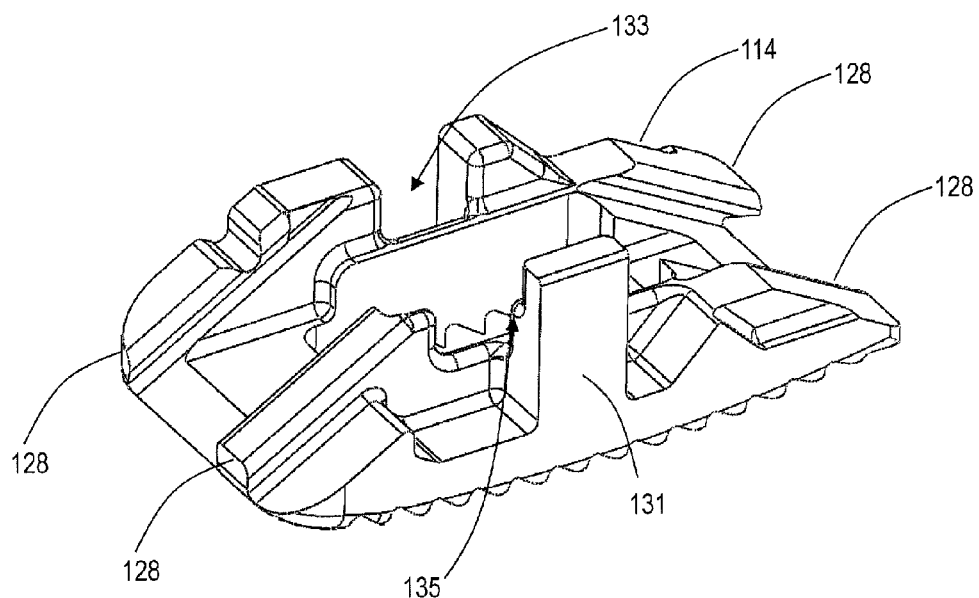
FIGS. 23a and 23b are perspective views of the superior and inferior members of an alternative exemplary embodiment of the expandable intervertebral implant of the present invention.
Figure 23B:
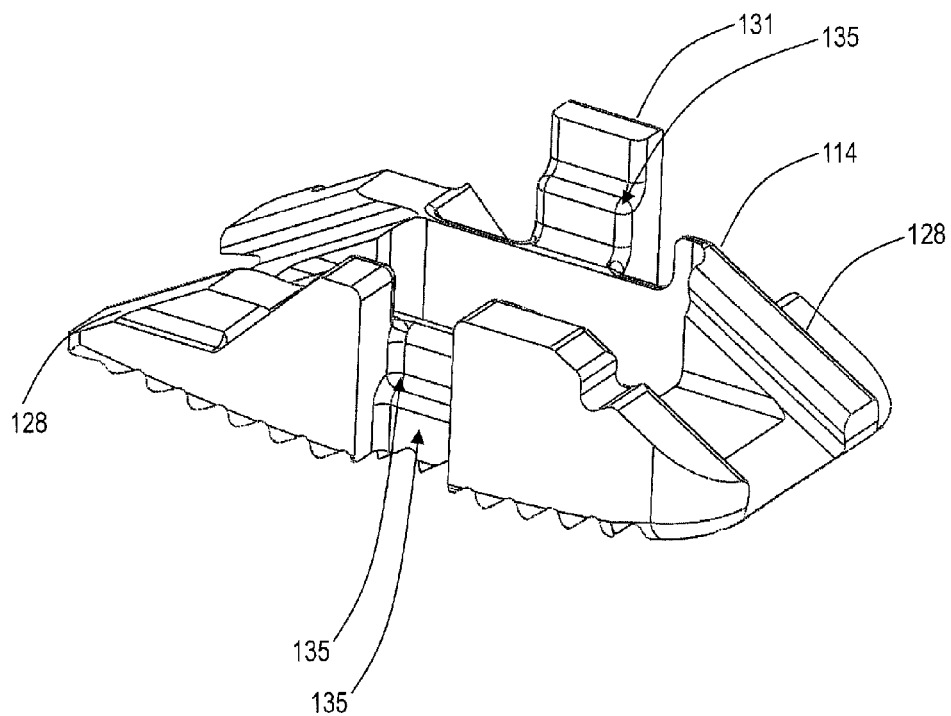
Figure 24A:
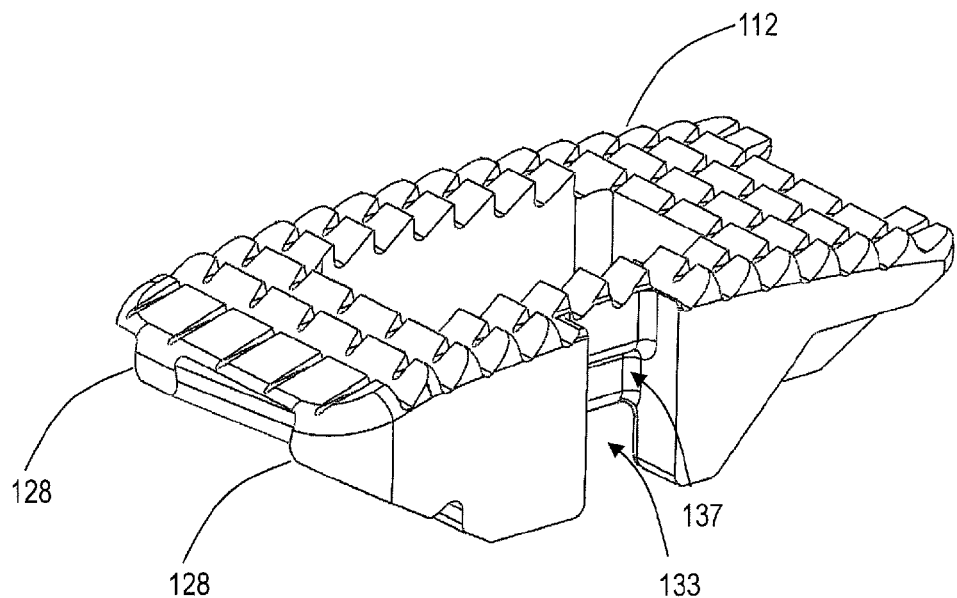
FIGS. 24a and 24b are additional perspective views of the superior and inferior members of an alternative exemplary embodiment of the expandable intervertebral implant of the present invention.
Figure 24B:
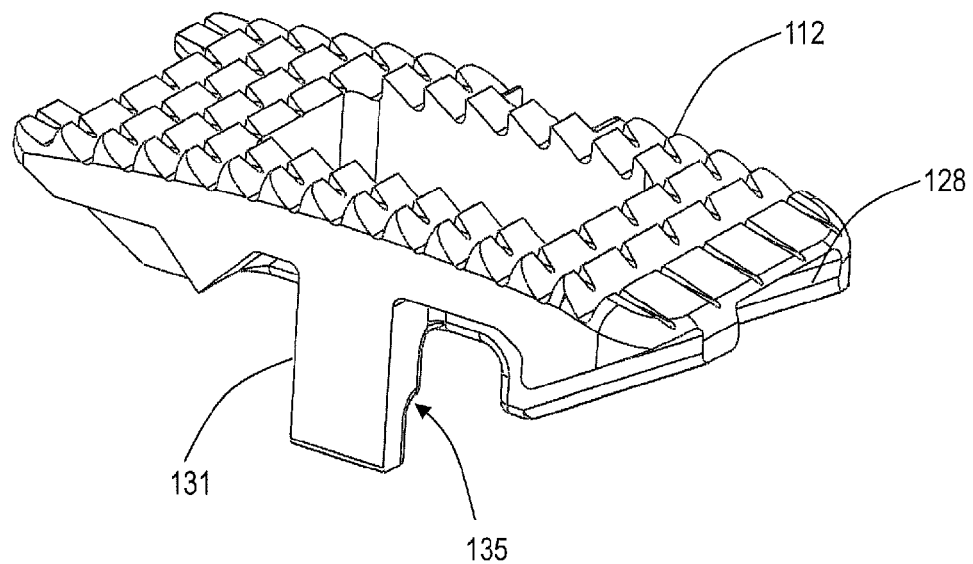
Figure 25:
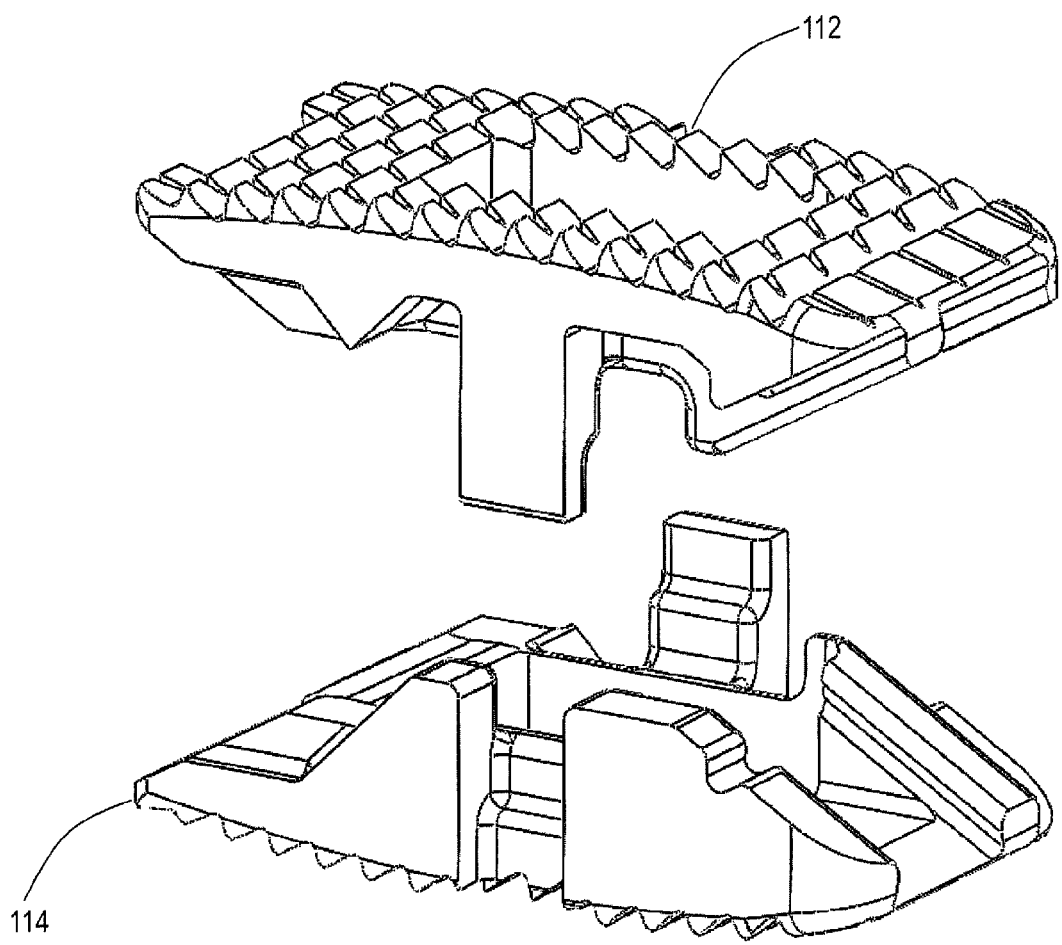
FIG. 25 is an additional perspective view of the superior and inferior members of an alternative exemplary embodiment of the expandable intervertebral implant of the present invention.
Figure 26:
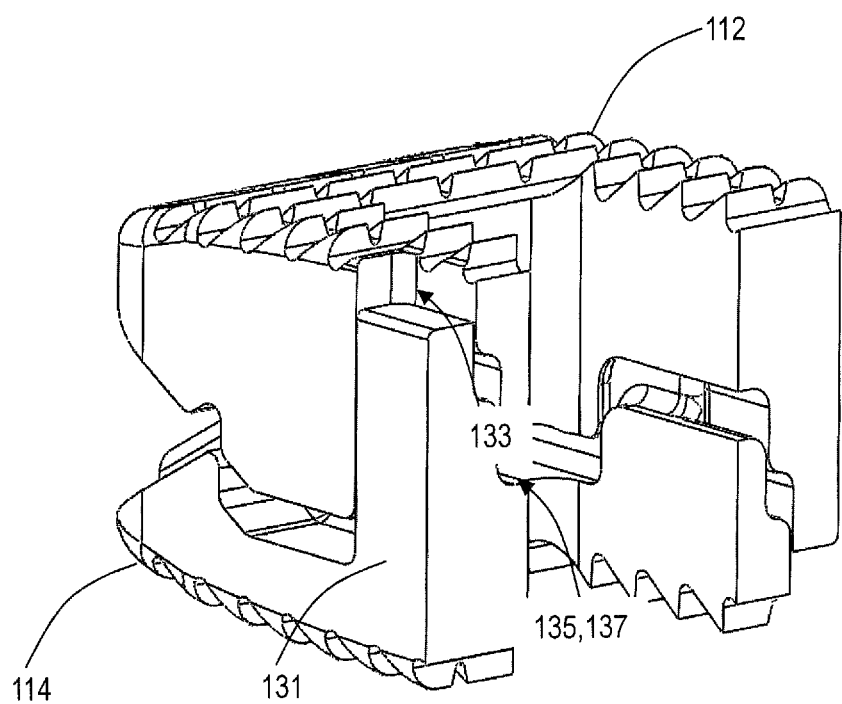
FIG. 26 is a partial perspective view of the superior and inferior members of an alternative exemplary embodiment of the expandable intervertebral implant of the present invention in an assembled configuration (see also FIGS. 22a and 22b for partial planar views of the same)
Figure 27A:
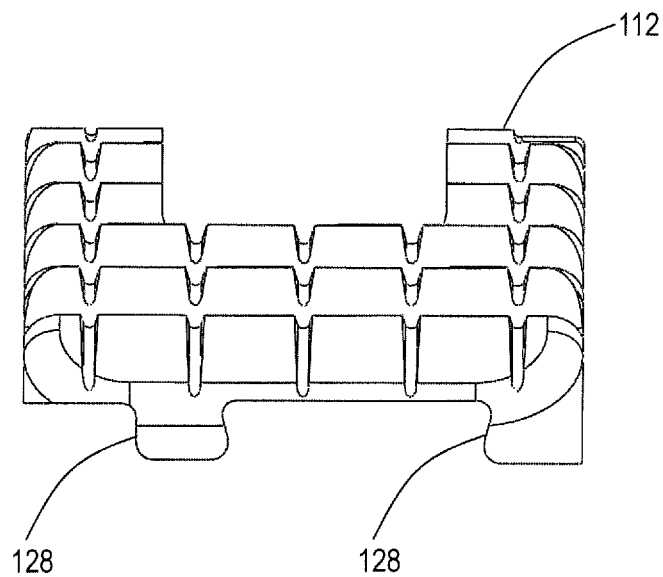
FIGS. 27a and 27b are end planar views of the superior member and the distal wedge structure of an alternative exemplary embodiment of the expandable intervertebral implant of the present invention, respectively.
Figure 27B:
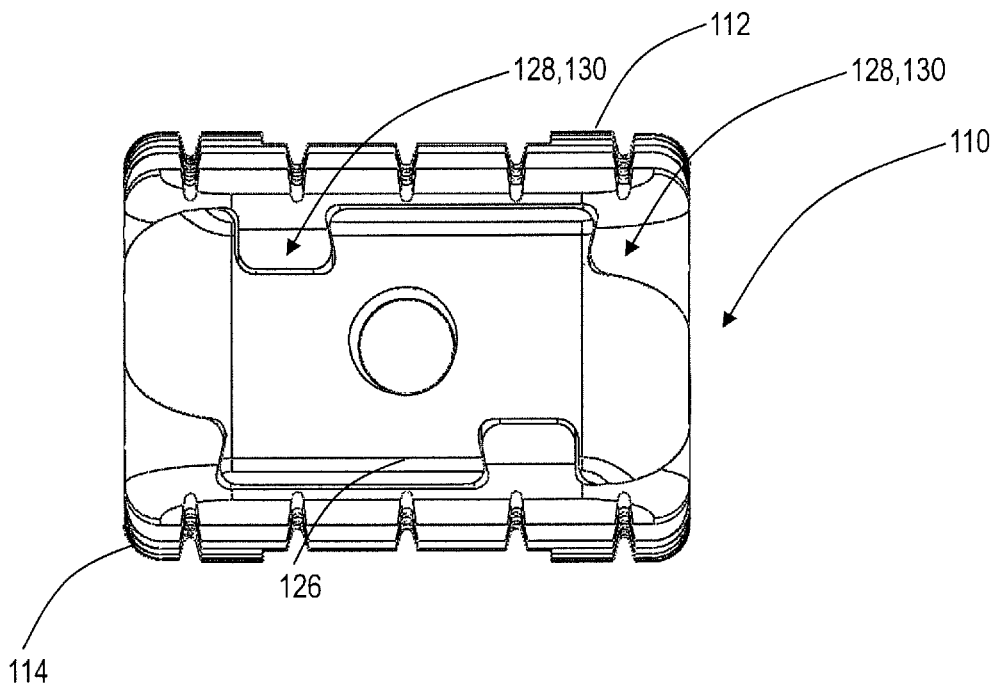
Figure 28A:
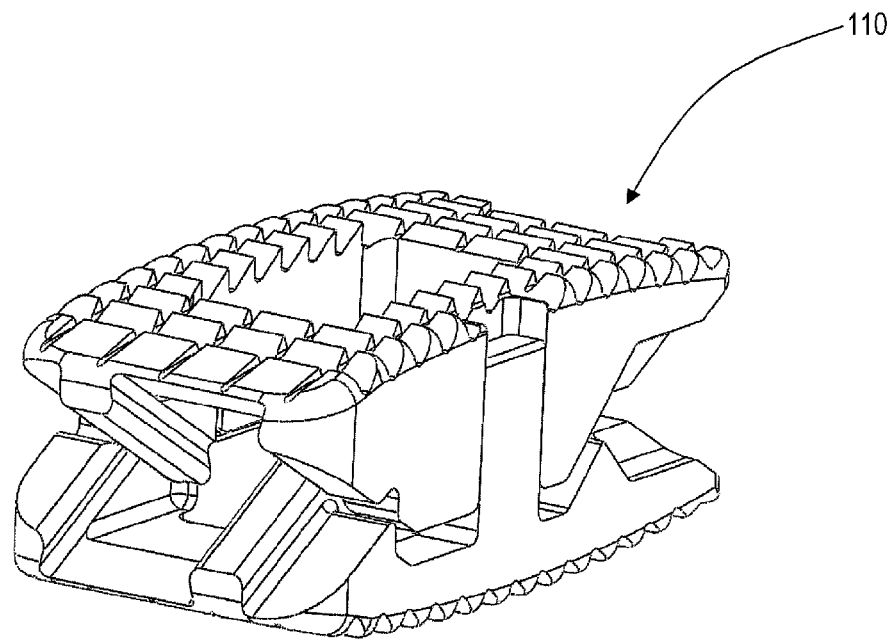
FIGS. 28a and 28b are perspective views of the superior and inferior members of an alternative exemplary embodiment of the expandable intervertebral implant of the present invention in an assembled configuration, both without and with the associated proximal and distal wedge structures in place, respectively.
Figure 28B:
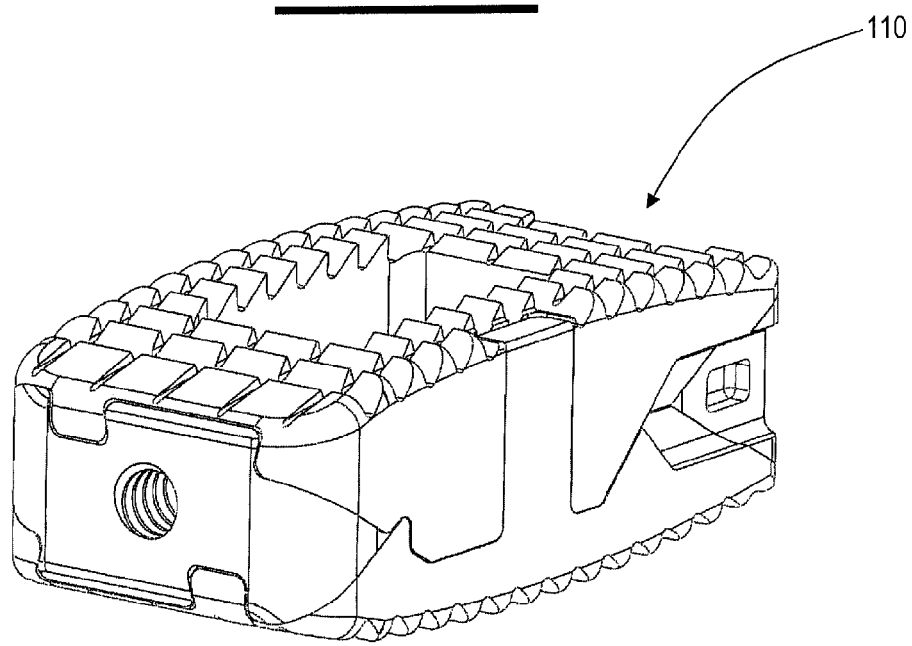

Referring to FIGS. 21a and 21b, preferably, the proximal and distal wedge structures 125 and 126 are disposed within the footprint(s) of the superior member 112 and the inferior member 114 in both the fully unexpanded and fully expanded states—meaning that the expandable intervertebral implant 110 has a known and constant or predictable size, which is a great advantage to an implanting surgeon. The superior member 112 and the inferior member 114 each (or collectively) define an internal space in which the actuation bolt 122 is disposed. This nesting of the actuation bolt 122 within the superior member 112 and the inferior member 114 provides the expandable intervertebral implant 110 with the smallest possible form factor when undeployed, allowing the superior member 112 and the inferior member 114 to collapse together, without interference from the actuation bolt 122. The proximal wedge structure 125 has a corresponding bore portion through which the actuation bolt 122 passes, while the distal wedge structure 126 has a corresponding threaded hole portion through which the actuation bolt 122 passes. This configuration permits the proximal and distal wedge structures 125 and 126 to translate smoothly along the central axis of the expandable intervertebral implant 110 with rotation of the actuation bolt 122, distracting the superior member 112 and the inferior member 114. One or more stabilization members 131 protruding from either or both of the superior member 112 and/or the inferior member 114 and engaging a corresponding stabilization recess 133 manufactured in the side of the other member 112 or 114 securely hold the superior member 112 and the inferior member 114 in a fixed translational alignment and prevent undesirable slipping between the two in any direction, as well as undesirable rotation or tilting. Thus, the expandable intervertebral implant 110 will predictably expand upon deployment, as opposed to "clam-shelling," for example.

Referring to FIGS. 22a, 22b, 23a, 23b, 24a, 24b, 25, and 26, in the exemplary embodiment illustrated, the superior member 112 and the inferior member 114 are essentially mirror images of one another, such that manufacturing, inventory, and assembly costs are minimized, although this is not strictly required. Furthermore, in this exemplary embodiment, the superior member 112 and the inferior member 114 are the same part, designed to nest with itself when rotated 180 degrees, such that manufacturing efficiencies are increased and production and inventory costs are minimized. As described above, one or more stabilization members 131 protruding from either or both of the superior member 112 and/or the inferior member 114 and engaging a corresponding stabilization recess 133 manufactured in the side of the other member 112 or 114 securely hold the superior member 112 and the inferior member 114 in a fixed translational alignment and prevent undesirable slipping between the two in any direction, as well as undesirable rotation or tilting.

Each of the stabilization members 131 includes a horizontal shelf structure 135 manufactured into the interior portion thereof This horizontal shelf structure 135 is configured to mate with a corresponding horizontal shelf structure 137 manufactured into an exterior portion of each of the stabilization recesses 133. Together these shelf structures 135 and 137 impart significant stability when the superior member 112 and the inferior member 114 are mated, and provide a stopping point for collapse of the superior member 112 and the inferior member 114 together vertically. Each of the proximal ramp portions 113 and 115 and the distal ramp portions 117 and 119 of the superior member 112 and the inferior member 114, respectively, includes one or more raised parallel rail structures 128 that run from the central portion of the expandable intervertebral implant 110 to the respective end portion of the expandable intervertebral implant 110. These raised parallel rail structures 128 are positioned and configured to engage corresponding recessed parallel slot structures 130 of the proximal and distal wedge structures 125 and 126 (see FIGS. 27a, 27b, 28a, 28b, 29a, 29b, 32a, and 32b). Preferably, each of the rail structures 128 and/or slot structures 130 includes a lip structure and/or is "dove-tailed" on one or both sides, such that the rail structures 128 and slot structures 130 are allowed to translate with respect to one another, but are prevented from disengaging one another all together. The rail structures 128 and slot structures 130 are staggered or offset such that the proximal ramp portions 113 and 115 and the distal ramp portions 117 and 119 of the superior member 112 and the inferior member 114 and the proximal and distal wedge structures 125 and 126 are "nested" when assembled, such that the form factor (i.e. both the vertical cross-section and the horizontal footprint) of the expandable intervertebral implant 110 is minimized when undeployed (i.e. unexpanded). This allows the track structures of the superior member 112 and the inferior member 114 to be longer (versus vertically aligned tracks), thereby permitting the wedge structures 125 and 126 of a fully contracted (i.e. fully unexpanded) implant 110 to be disposed within the horizontal footprint of the superior member 112 and the inferior member 114 while maintaining minimum wedge translation (i.e. travel) length requirements to effect the required distraction of the implant 110. Again, this makes the assembly as compact as possible, with the smallest possible undeployed vertical cross-section and the smallest/shortest possible undeployed horizontal footprint. Again, this also allows the proximal and distal wedge structures 125 and 126 to be disposed within the footprint(s) of the superior member 112 and the inferior member 114 in the fully unexpanded state—meaning that the expandable intervertebral implant 110 has a known and constant or predictable size, which is a great advantage to an implanting surgeon. Further, this configuration preserves the integrity and continuity of the leading (i.e. distal) edge of the superior member 112 and the inferior member 114, and allows the proximal ramp portions 113 and 115 and the distal ramp portions 117 and 119 to be made longer, without the rail structures 128 interfering with one another, thereby increasing bony surface purchase area.

Figure 29A:
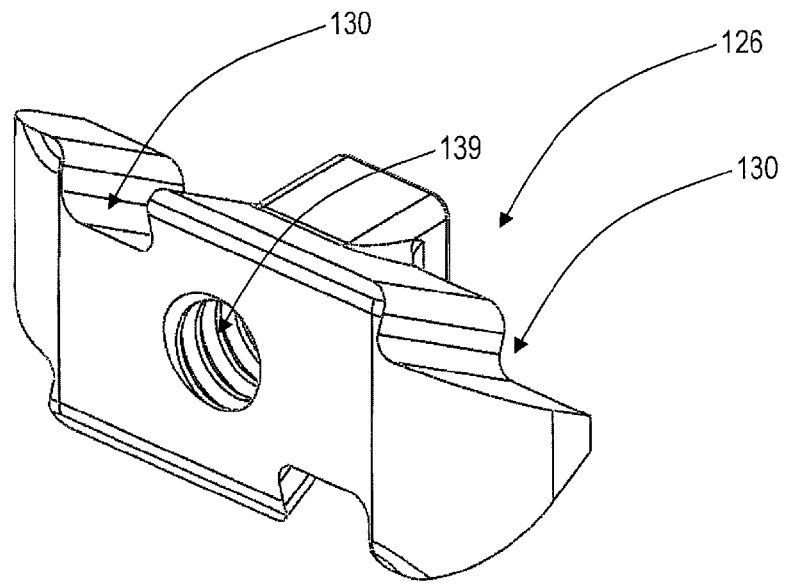
FIGS. 29a and 29b are perspective views of the distal wedge structure of an alternative exemplary embodiment of the expandable intervertebral implant of the present invention.
Figure 29B:
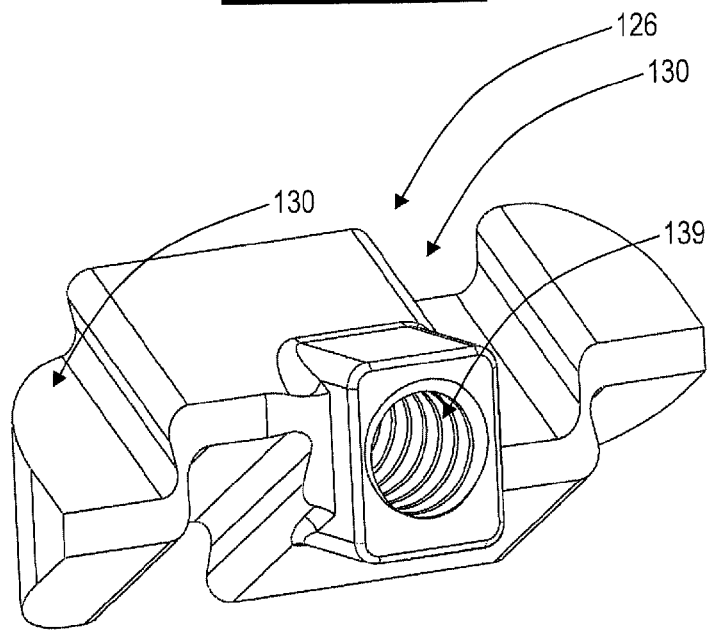

FIGS. 29a and 29b further illustrate the distal wedge structure 126 of this alternative embodiment of the expandable intervertebral implant 110 of the present invention, highlighting the configuration of the slot structures 130 and threaded bore 139.

Figure 30A:
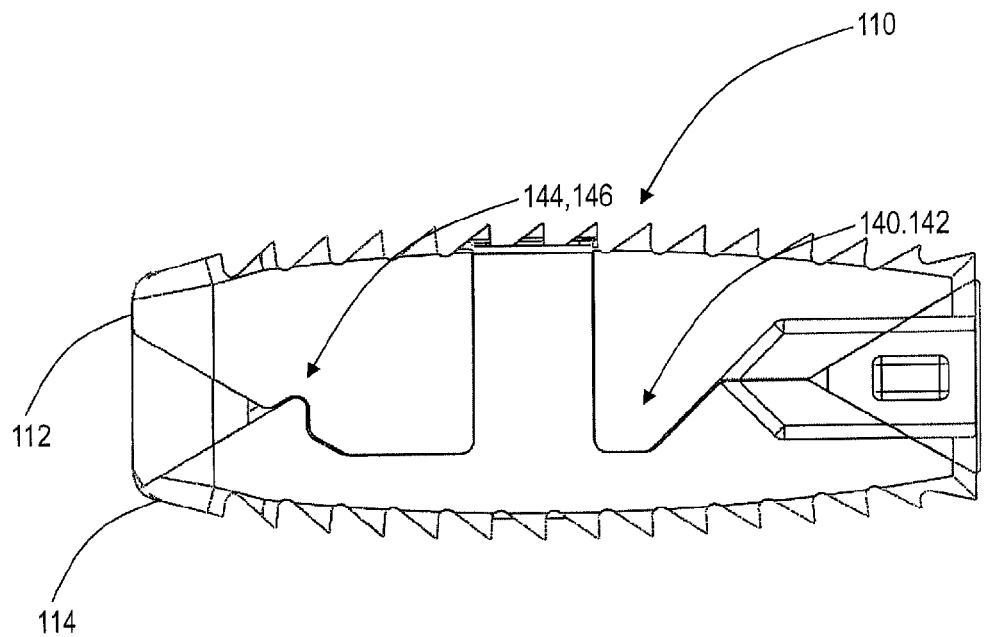
FIGS. 30a and 30b are side planar views of an alternative exemplary embodiment of the expandable intervertebral implant of the present invention in both unexpanded and partially or wholly expanded configurations.
Figure 30B:
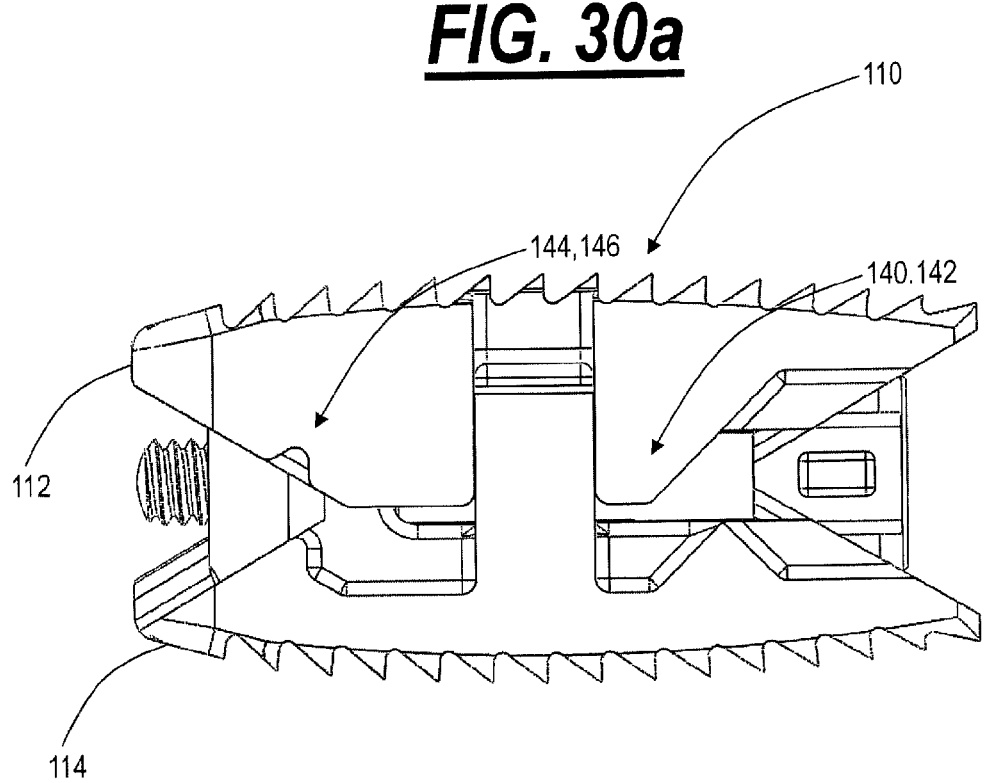

Referring to FIGS. 30a and 30b, the superior member 112 includes one or more downward projecting portions 140 on one side thereof (in the exemplary embodiment illustrated). The inferior member 114 includes one or more corresponding recesses 142 on one side thereof (in the exemplary embodiment illustrated). When the expandable intervertebral implant 110 is in its collapsed state, these features act as a locking mechanism, increasing implant shear strength and overall stability during delivery and positioning in the intervertebral space, which may require the use of a slap hammer or other similar striking instrument. Similar locking tabs 144 and notches 146 may also be used for this purpose in a variety of configurations.

Figure 31A:
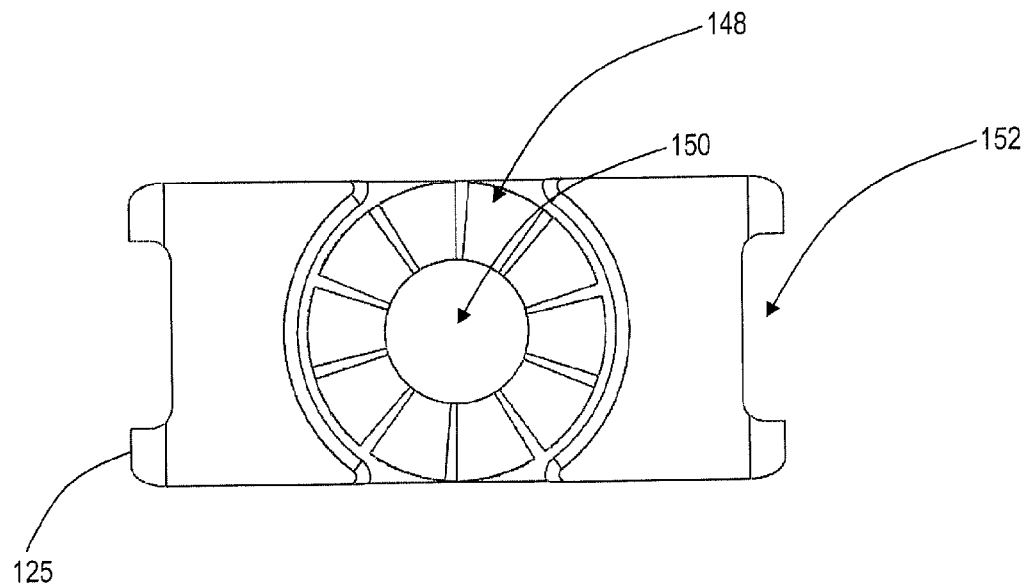
FIGS. 31a and 31b are end planar views of the proximal wedge structure of an alternative exemplary embodiment of the expandable intervertebral implant of the present invention.
Figure 31B:
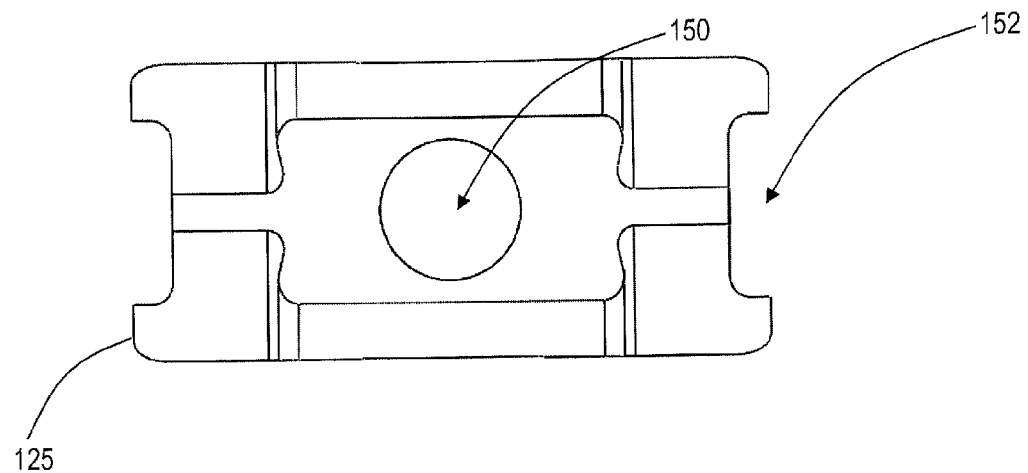
Figure 32A:
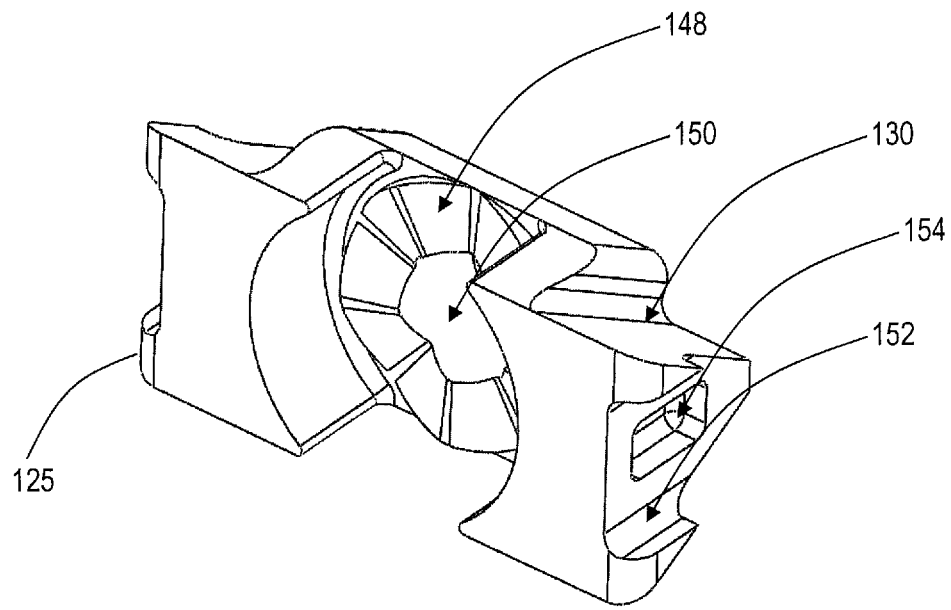
FIGS. 32a and 32b are perspective views of the proximal wedge structure of an alternative exemplary embodiment of the expandable intervertebral implant of the present invention.
Figure 32B:
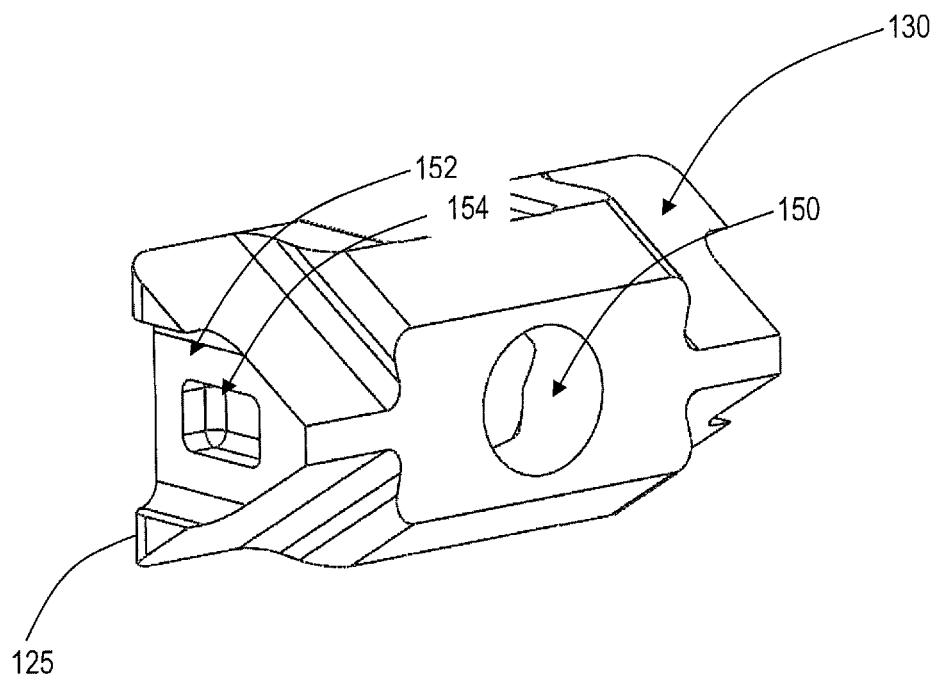

Referring to FIGS. 31a and 31b, the proximal wedge structure 125 includes a recessed radial spline 148 (or spiral jaw clutch mechanism) disposed around the central bore 150, such that the expandable intervertebral implant 110 may be expanded in a "ratcheted" manner (i.e. incrementally) and securely hold a given degree of expansion. This "ratcheted" expansion may be reversed for repositioning and redeployment. The recessed nature of the radial spline 148 again reduces the overall footprint of the expandable intervertebral implant 110, accepting and "hiding" the head portion of the actuation bolt 122. Further, the sides of the proximal wedge structure 125 include grooves 152 and recessed pockets 154 that are configured to receive various grasping and deployment tools, as described in greater detail herein below.

Figure 33A:
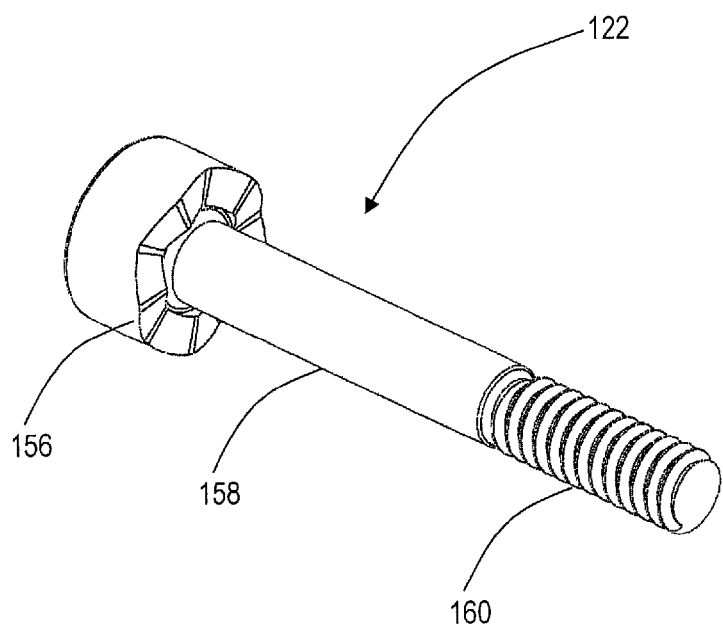
FIGS. 33a and 33b are perspective views of the actuation bolt of an alternative exemplary embodiment of the expandable intervertebral implant of the present invention.
Figure 33B:
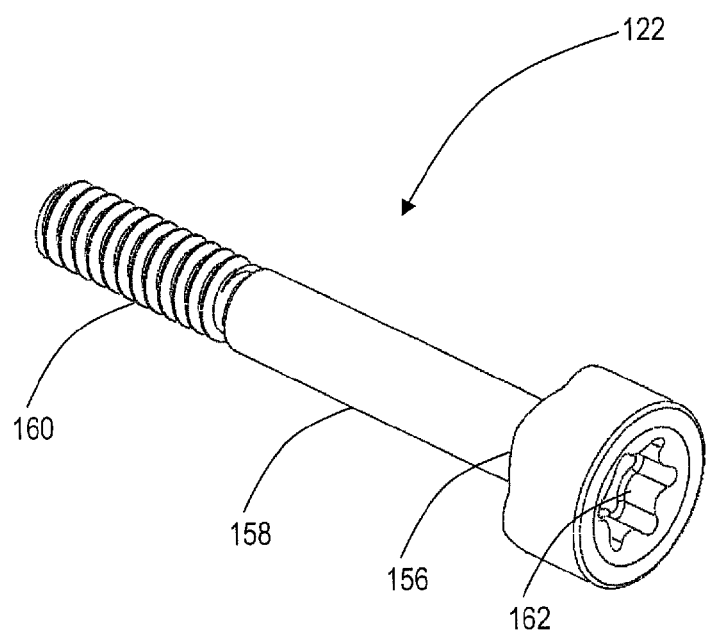
Figure 34:
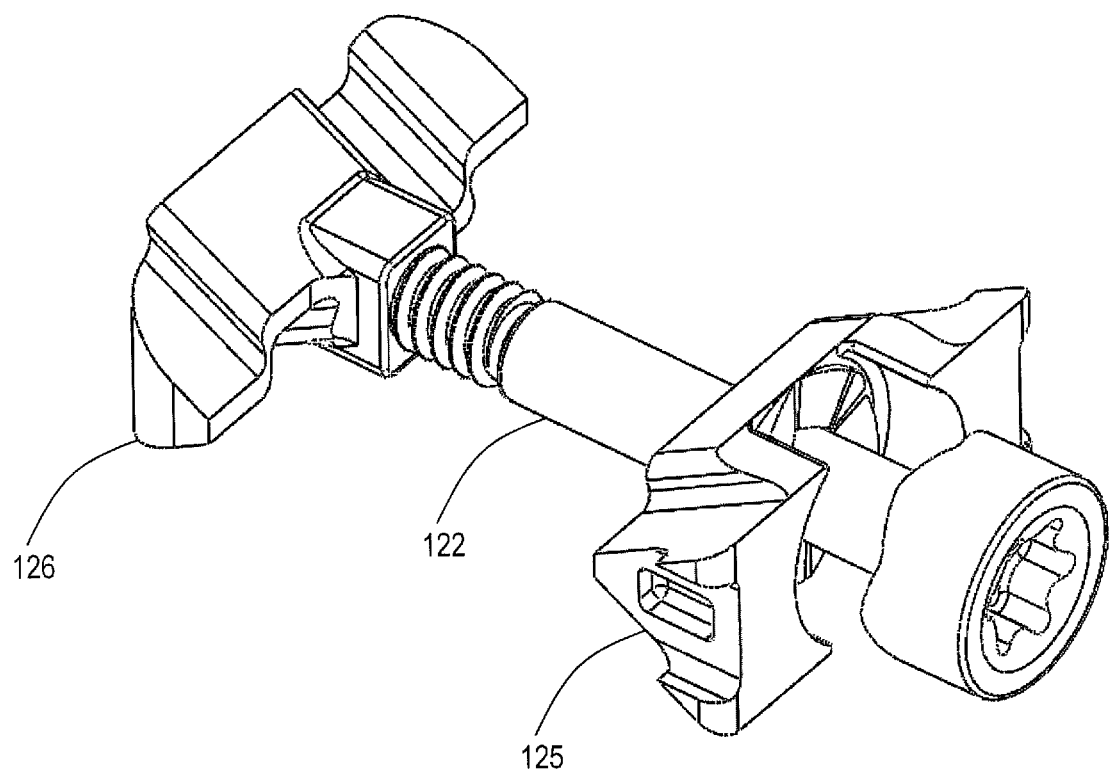
FIG. 34 is a perspective view of the proximal wedge structure, the distal wedge structure, and the actuation bolt of an alternative exemplary embodiment of the expandable intervertebral implant of the present invention in an assembled configuration.
Figure 35:
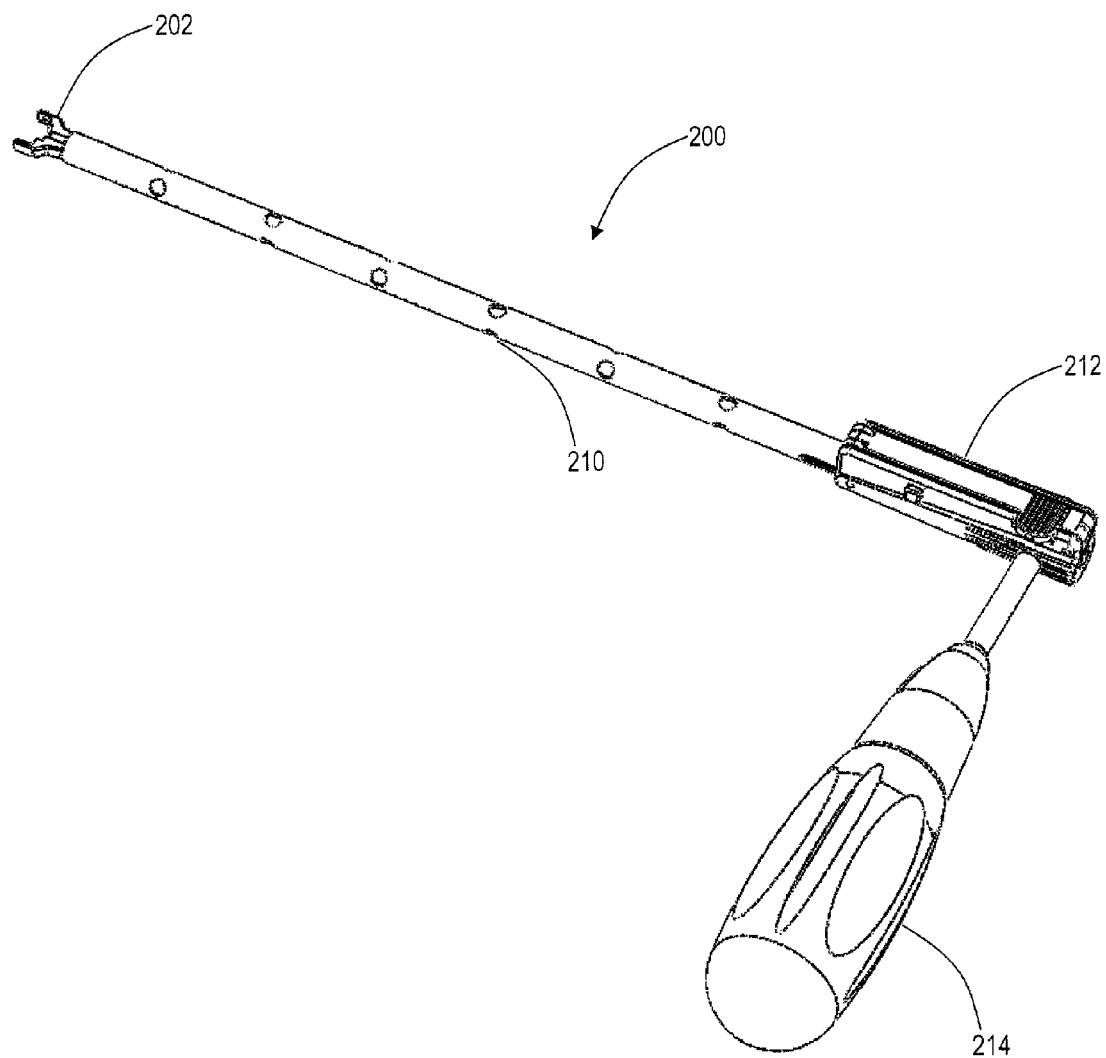
FIG. 35 is a perspective view of the implant inserter tool used to insert an alternative exemplary embodiment of the expandable intervertebral implant of the present invention.
Figure 36A:
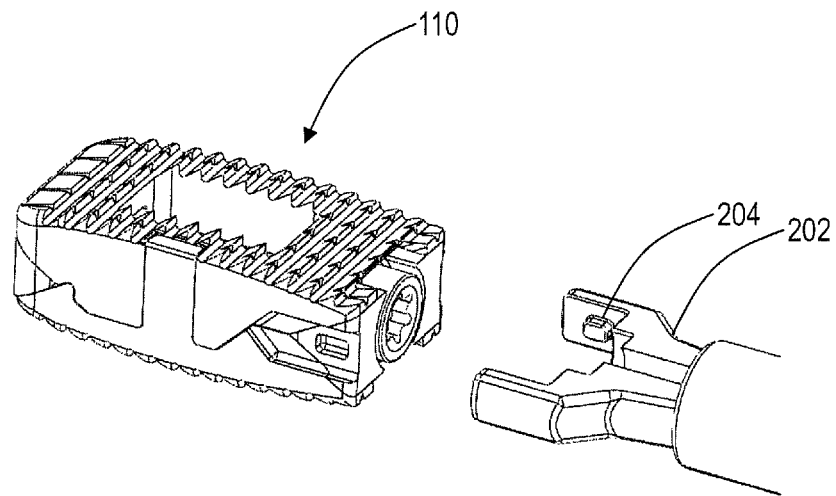
FIGS. 36a and 36b are perspective views of an end portion of the implant inserter tool used to insert an alternative exemplary embodiment of the expandable intervertebral implant of the present invention, both disengaged from and engaged with the expandable intervertebral implant, respectively.
Figure 36B:
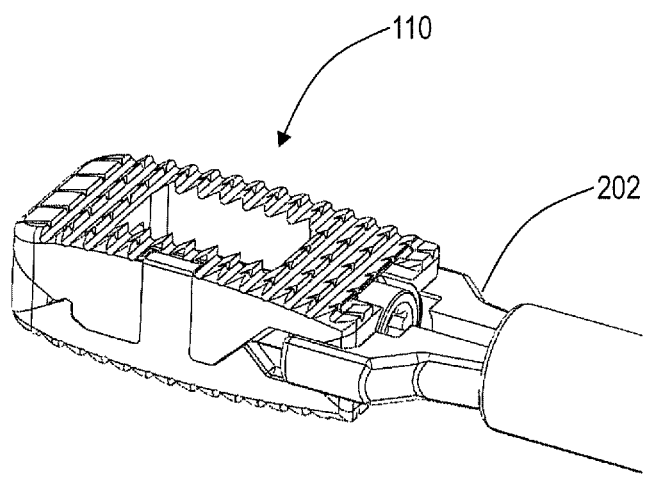
Figure 37A:
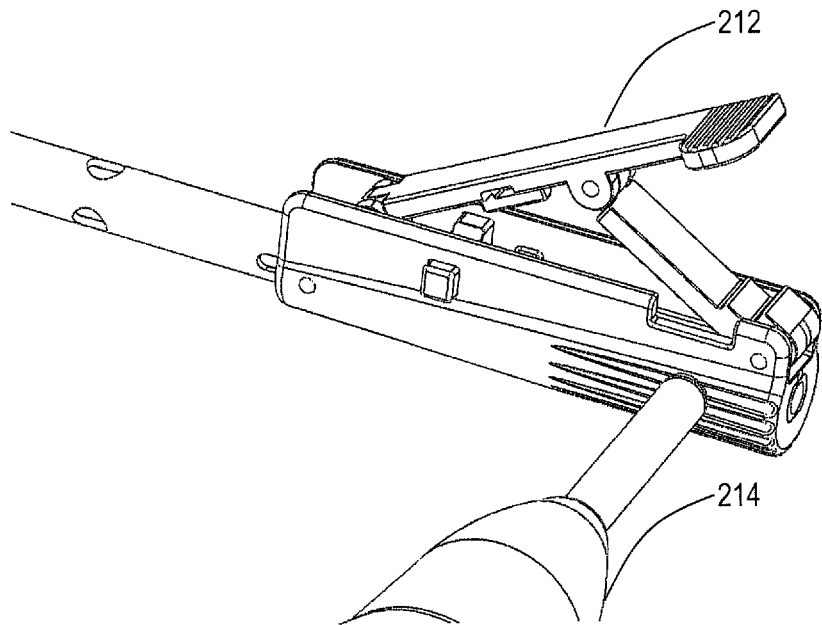
FIGS. 37a and 37b are perspective views of another end portion of the implant inserter tool used to insert an alternative exemplary embodiment of the expandable intervertebral implant of the present invention, both in unlocked and locked configurations, respectively.
Figure 37B:
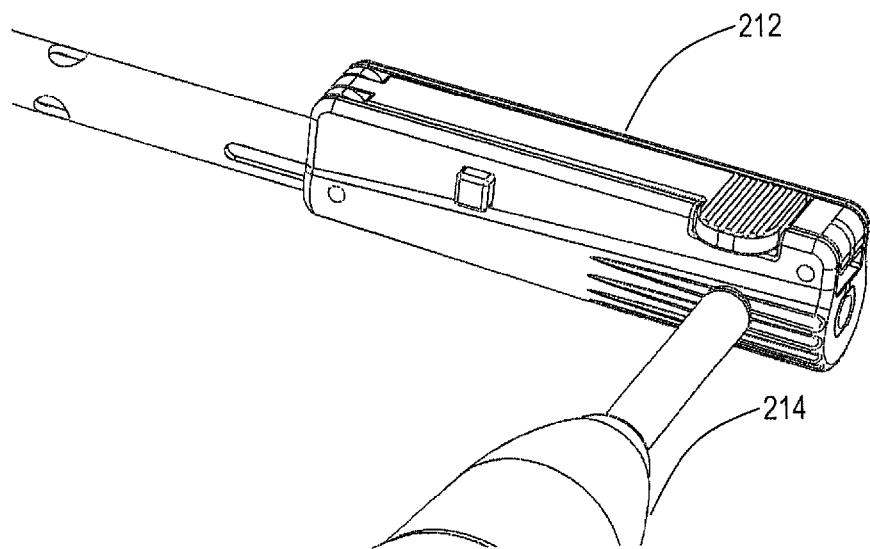
Figure 38A:
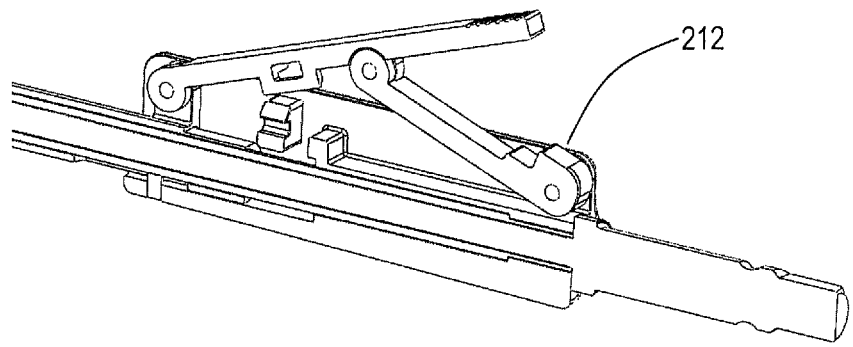
FIGS. 38a and 38b are partial perspective views of another end portion of the implant inserter tool used to insert an alternative exemplary embodiment of the expandable intervertebral implant of the present invention, both in unlocked and locked configurations, respectively.
Figure 38B:
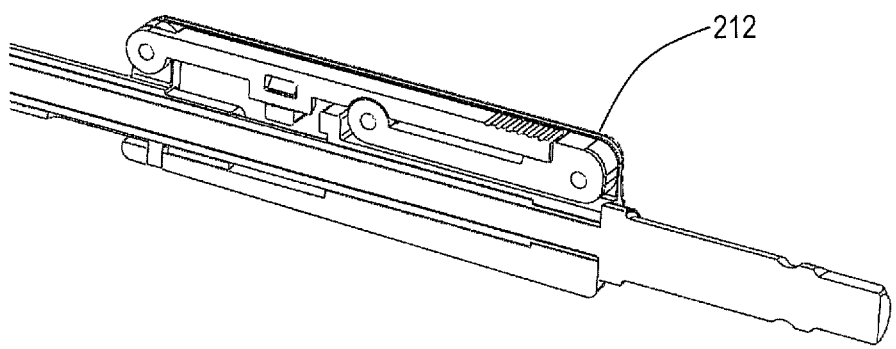
Figure 39:
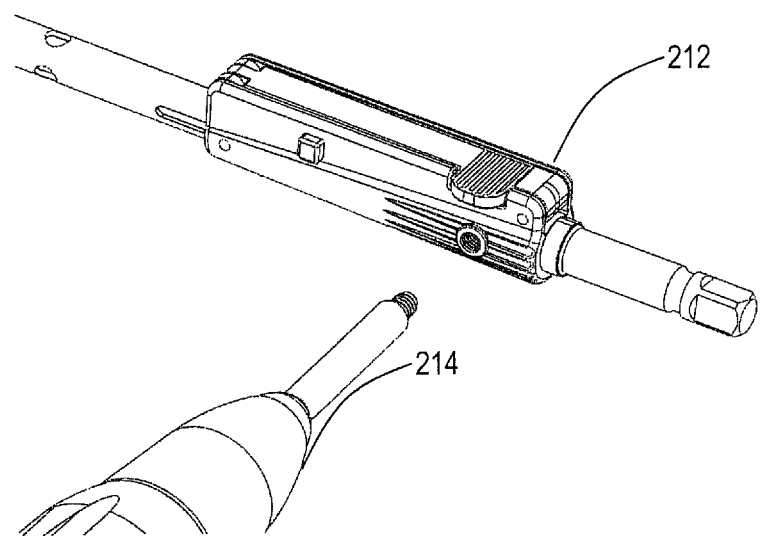
FIG. 39 is a perspective view of another end portion of the implant inserter tool used to insert an alternative exemplary embodiment of the expandable intervertebral implant of the present invention, highlighting the engagement of the associated handle assembly.
Figure 40:
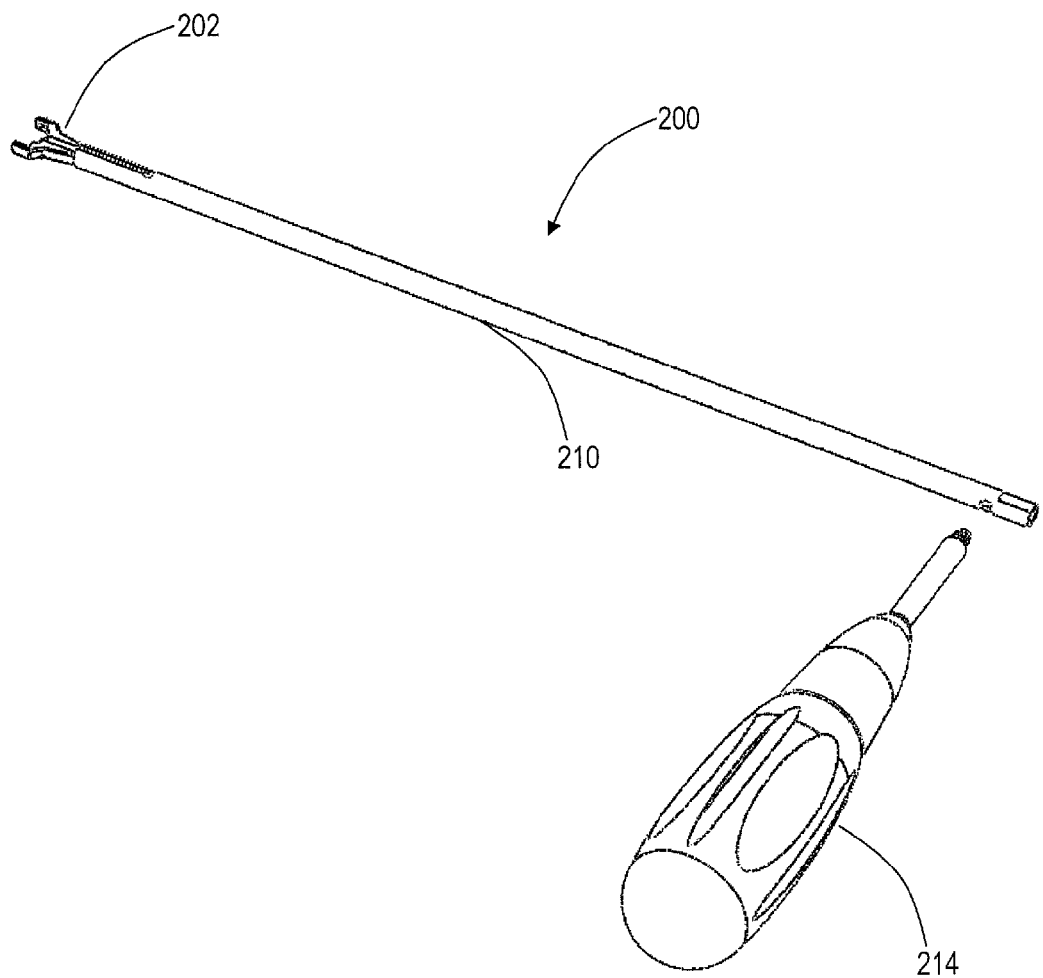
FIG. 40 is a perspective view of the implant inserter tool used to insert an alternative exemplary embodiment of the expandable intervertebral implant of the present invention, highlighting the engagement of the associated handle assembly.

Referring to FIGS. 33a and 33b, the actuation bolt 122 includes a complimentary radial spline 156 on the back side of the head portion, a smooth shaft portion 158 for passing through the proximal wedge structure 125, and a threaded portion 160 for engaging the distal wedge structure 126. This assembly is illustrated in FIG. 34. The head portion of the actuation bolt 122 also includes a keyed recess 162 for receiving a driver, such as a hexalobular driver, by which the actuation bolt 122 is rotated to translate the proximal and/or distal wedge structure(s) 125 and 126. As is described in greater detail herein below, the driver and holding/placement tool may be incorporated into one assembly, such that the expandable intervertebral implant 110 may be grasped, positioned, expanded, and released in a series of simple steps, by a single surgeon, using a single tool.

Referring to FIGS. 35, 36a, 36b, 37a, 37b, 38a, 38b, 39, 40, 42, 43, 44a, and 44b, in an alternative exemplary embodiment, the combination placement/deployment tool 200 of the present invention includes a pair of movable elongate arms 202 that each have an interior retention structure 204 that is configured to selectively and releasably engage the corresponding recessed pocket 154 of the expandable intervertebral implant 110 in an anti-rotational manner. The combination placement/deployment tool 200 also includes a driver disposed between the pair of elongate arms 202 that is configured to selectively and releasably engage the keyed recess 162 of the actuation bolt 122. When rotated, the driver rotates the actuation bolt 122, thereby translating the wedge structures 125 and 126 and expanding/contracting the superior member 112 and the inferior member 114 of the expandable intervertebral implant 110. The elongate arms 202 are engaged/released via the actuation of a lever mechanism 212 disposed at the opposite end of an elongate shaft 210. The combination placement/deployment tool 200 further includes a handle 214 (e.g. an MIS side handle) for grasping and a socket 216 (e.g. a torque limiting handle) for rotating the driver. It will be readily apparent to those of ordinary skill in the art that the expandable intervertebral implant 110 of the present invention may be placed via an open surgical procedure, or via any suitable minimally-invasive portal-type of system.

Figure 41A:
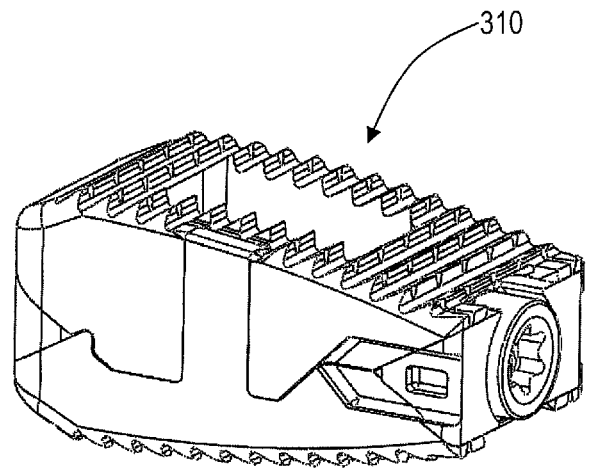
FIGS. 41a and 41b are perspective views of another alternative exemplary embodiment of the expandable intervertebral implant of the present invention in an unexpanded configuration.
Figure 41B:
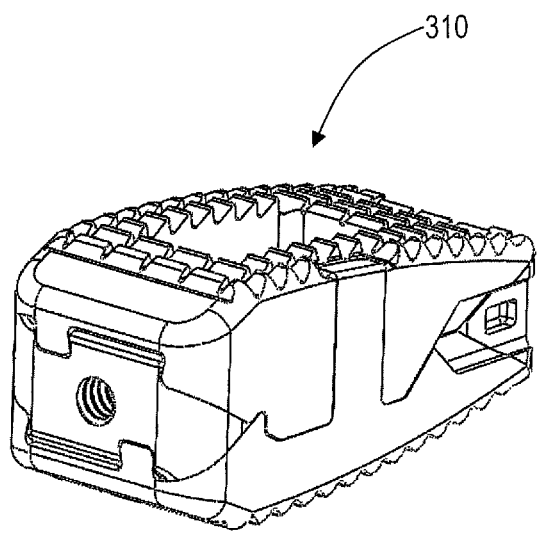
Figure 42:
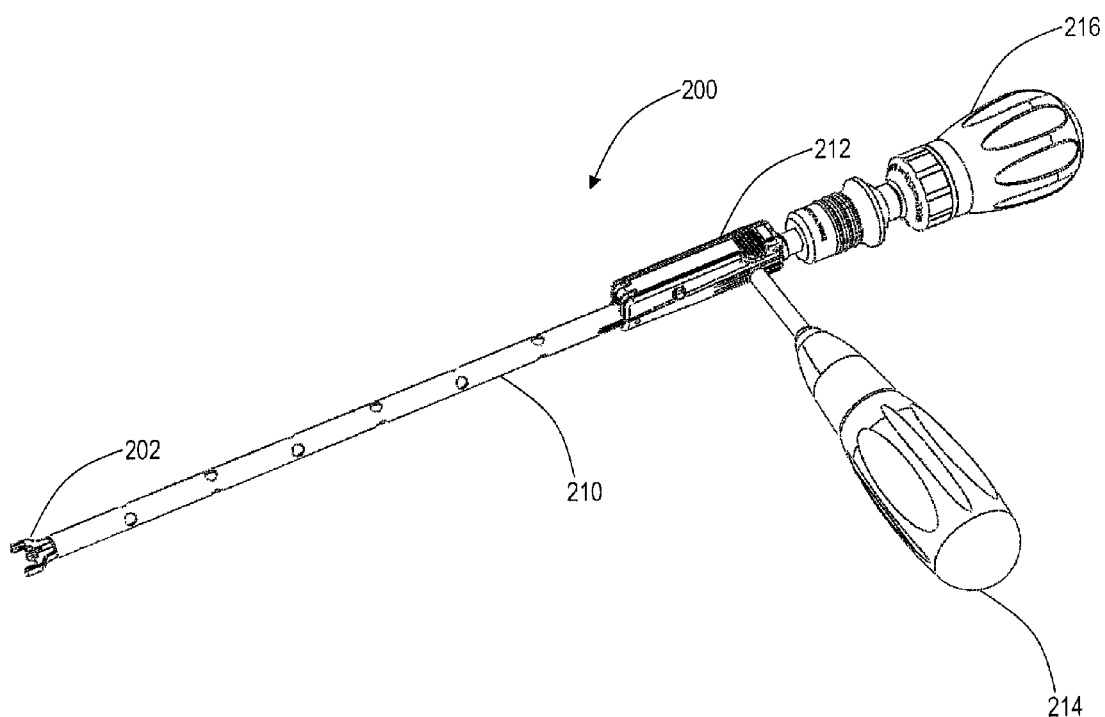
FIG. 42 is a perspective view of the implant inserter tool used to insert an alternative exemplary embodiment of the expandable intervertebral implant of the present invention, highlighting the engagement of the associated handle assembly and actuation handle assembly.
Figure 43:
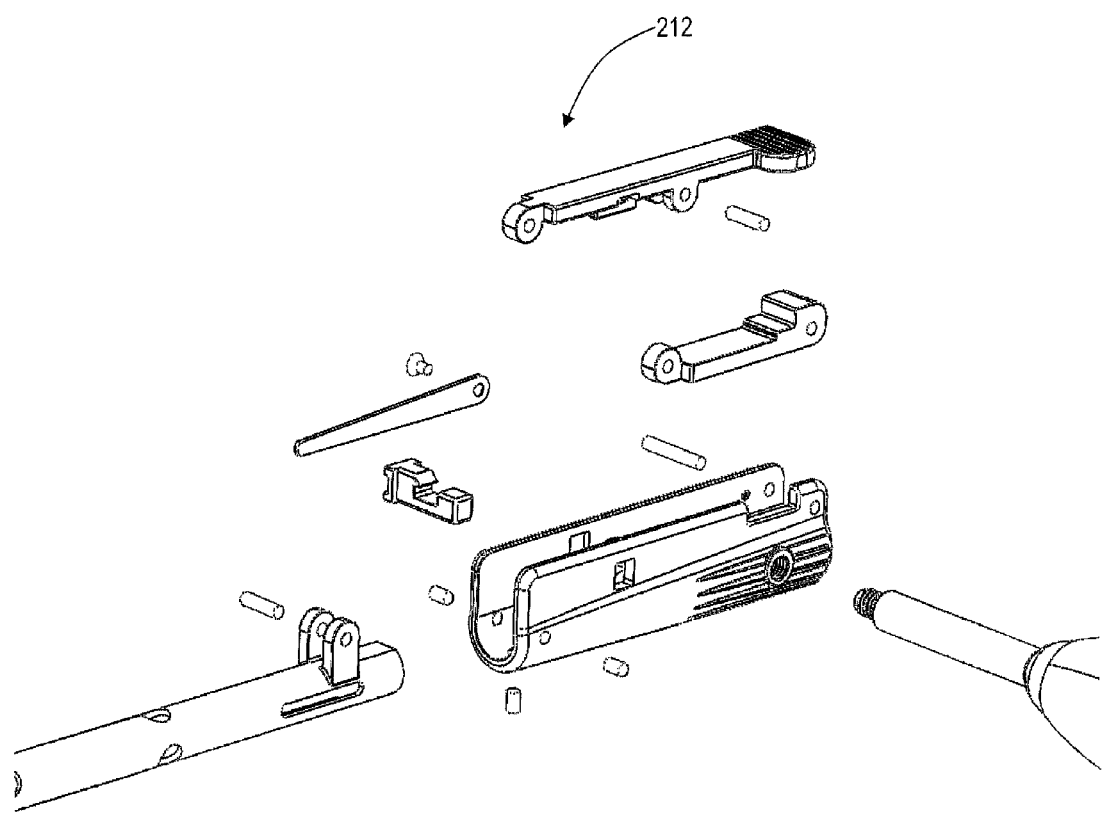
FIG. 43 is an exploded perspective view of another end portion of the implant inserter tool used to insert alternative exemplary embodiments of the expandable intervertebral implant of the present invention.
Figure 44A:
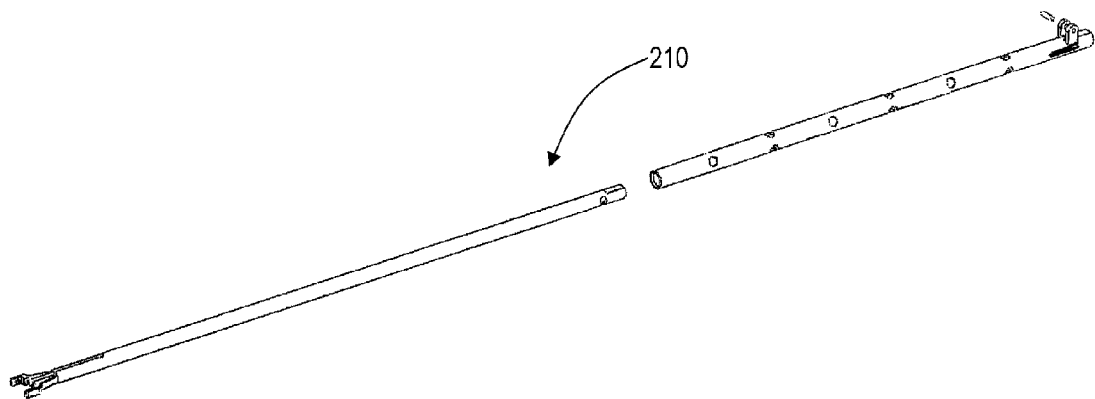
FIGS. 44a and 44b are perspective views of the implant inserter tool used to insert alternative exemplary embodiments of the expandable intervertebral implant of the present invention.
Figure 44B:
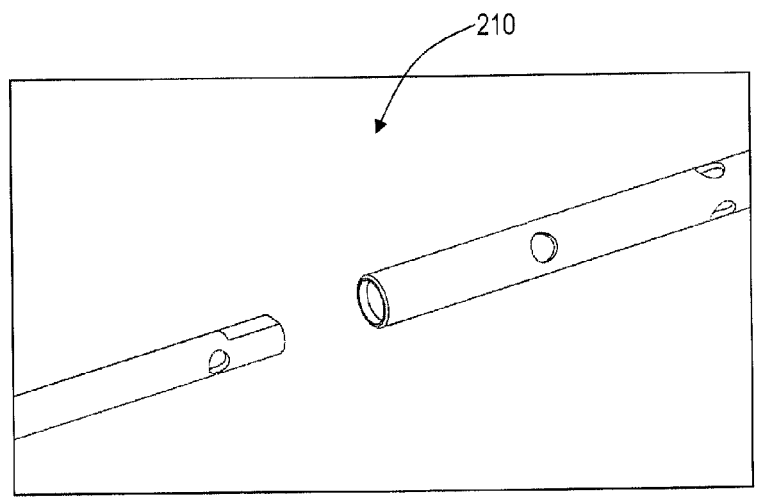

As an alternative, FIGS. 41a and 41b illustrate a lordotic version of the expandable intervertebral implant 310 of the present invention—which is "thicker" at one end than at the other end, similar to embodiments described above. This is advantageous for TLIF and ALIF procedures. Side slope versions may also be produced for DLIF procedures, for example.

Although the expandable intervertebral implant of the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples fall within the spirit and scope of the present invention, are contemplated thereby, and are intended to be covered by the following claims.

What is claimed is:

1. An expandable intervertebral implant, comprising:
a superior member configured to engage a superior intervertebral body;
an inferior member configured to engage an inferior intervertebral body; and
an expansion mechanism disposed between the superior member and the inferior member configured to selectively adjust a vertical separation of the superior member from the inferior member;
wherein the expansion mechanism comprises a proximal wedge structure and a distal wedge structure that are relatively translated between the superior member and the inferior member, wherein the proximal wedge structure and the distal wedge structure are each coupled to the superior member and the inferior member by a plurality of track structures and rail structures, and
wherein the superior member and the inferior member each comprise a pair of rails, wherein the rails of the superior member are horizontally offset in the same direction from the rails of the inferior member such that each rail of the superior member is disposed substantially side-by-side horizontally adjacent to a respective one of the rails of the inferior member when the expandable vertebral implant is in an unexpanded configuration, and wherein one rail of the superior member is disposed between an associated rail of the inferior member and a central axis of the implant and another rail of the inferior member is disposed between the associated rail of the superior member and the central axis of the implant in the unexpanded configuration.

2. The expandable intervertebral implant of claim 1, wherein one or more track structures and rail structures associated with a top surface of the distal wedge structure are offset horizontally with respect to one or more track structures and rail structures associated with a bottom surface of the distal wedge structure.

3. The expandable intervertebral implant of claim 1, wherein one or more track structures and rail structures associated with a top surface of the proximal wedge structure are offset horizontally with respect to one or more track structures and rail structures associated with a bottom surface of the proximal wedge structure.

4. The expandable intervertebral implant of claim 1, wherein the expansion mechanism further comprises an actuation bolt that passes through the proximal wedge structure and is coupled to the distal wedge structure and causes the wedge structures to relatively translate when rotated.

5. The expandable intervertebral implant of claim 1, wherein the superior member and the inferior member each comprise a plurality of ramp structures.

6. The expandable intervertebral implant of claim 5, wherein the superior member comprises a ramp structure that engages the proximal wedge structure and a ramp structure that engages the distal wedge structure.

7. The expandable intervertebral implant of claim 5, wherein the inferior member comprises a ramp structure that engages the proximal wedge structure and a ramp structure that engages the distal wedge structure.

8. The expandable intervertebral implant of claim 1, further comprising an elongate arm structure protruding from the superior member engaging a corresponding recess of the inferior member and an elongate arm structure protruding from the inferior member and engaging a corresponding recess of the superior member.

9. A surgical method, comprising:
providing an expandable intervertebral implant, comprising:
a superior member configured to engage a superior intervertebral body;
an inferior member configured to engage an inferior intervertebral body; and
an expansion mechanism disposed between the superior member and the inferior member configured to selectively adjust a vertical separation of the superior member from the inferior member;
wherein the expansion mechanism comprises a proximal wedge structure and a distal wedge structure that are relatively translated between the superior member and the inferior member, wherein the proximal wedge structure and the distal wedge structure are each coupled to the superior member and the inferior member by a plurality of track structures and rail structures,
wherein the superior member and the inferior member each comprise a pair of rails, wherein the rails of the superior member are horizontally offset in the same direction from the rails of the inferior member such that each rail of the superior member is disposed substantially side-by-side horizontally adjacent to a respective one of the rails of the inferior member when the expandable vertebral implant is in an unexpanded configuration, and wherein one rail of the superior member is disposed between an associated rail of the inferior member and a central axis of the implant and another rail of the inferior member is disposed between the associated rail of the superior member and the central axis of the implant in the unexpanded configuration; and
disposing the expandable intervertebral implant between the superior intervertebral body and the inferior intervertebral body; and
selectively adjusting the separation of the superior member and the inferior member, thereby selectively adjusting a distraction of the superior intervertebral body from the inferior intervertebral body.

10. The surgical method of claim 9, wherein one or more track structures and rail structures associated with a top surface of the distal wedge structure are offset horizontally with respect to one or more track structures and rail structures associated with a bottom surface of the distal wedge structure.

11. The surgical method of claim 9, wherein one or more track structures and rail structures associated with a top surface of the proximal wedge structure are offset horizontally with respect to one or more track structures and rail structures associated with a bottom surface of the proximal wedge structure.

12. The surgical method of claim 9, wherein the expansion mechanism further comprises an actuation bolt that passes through the proximal wedge structure and is coupled to the distal wedge structure and causes the wedge structures to relatively translate when rotated.

13. The surgical method of claim 9, wherein the superior member and the inferior member each comprise a plurality of ramp structures.

14. The surgical method of claim 13, wherein the superior member comprises a ramp structure that engages the proximal wedge structure and a ramp structure that engages the distal wedge structure.

15. The surgical method of claim 13, wherein the inferior member comprises a ramp structure that engages the proximal wedge structure and a ramp structure that engages the distal wedge structure.

16. The surgical method of claim 9, wherein the expandable intervertebral implant further comprises an elongate arm structure protruding from the superior member engaging a corresponding recess of the inferior member and an elongate arm structure protruding from the inferior member and engaging a corresponding recess of the superior member.

* * * * *